United States Patent
Panzner et al.

(10) Patent No.: US 9,677,073 B2
(45) Date of Patent: Jun. 13, 2017

(54) HYDROXYLATED POLYAMINE DERIVATIVES AS TRANSFECTION REAGENTS

(71) Applicant: Lipocalyx GmbH, Halle (DE)

(72) Inventors: Steffen Panzner, Halle (DE); Christian Reinsch, Halle (DE); Volkmar Wendisch, Dessau (DE); Christina Dreher, Halle (DE)

(*) Notice: Subject to any disclaimer, the term of this patent is extended or adjusted under 35 U.S.C. 154(b) by 0 days.

(21) Appl. No.: 14/432,327

(22) PCT Filed: Oct. 2, 2013

(86) PCT No.: PCT/EP2013/002978
§ 371 (c)(1),
(2) Date: Mar. 30, 2015

(87) PCT Pub. No.: WO2014/053245
PCT Pub. Date: Apr. 10, 2014

(65) Prior Publication Data
US 2015/0259678 A1 Sep. 17, 2015

(30) Foreign Application Priority Data
Oct. 5, 2012 (EP) .................................... 12006913

(51) Int. Cl.
*C12N 15/113* (2010.01)
*C08G 73/02* (2006.01)
*C08L 79/02* (2006.01)
*C12N 15/85* (2006.01)
*A61K 47/48* (2006.01)

(52) U.S. Cl.
CPC ...... *C12N 15/113* (2013.01); *A61K 47/48046* (2013.01); *A61K 47/48192* (2013.01); *A61K 47/48315* (2013.01); *C08G 73/0206* (2013.01); *C08L 79/02* (2013.01); *C12N 15/85* (2013.01); *C08L 2203/02* (2013.01); *C12N 2310/14* (2013.01); *C12N 2310/351* (2013.01); *C12N 2800/107* (2013.01)

(58) Field of Classification Search
None
See application file for complete search history.

(56) References Cited

U.S. PATENT DOCUMENTS

2003/0077827 A1  4/2003  Uhler
2006/0168739 A1* 8/2006  Caswell ................... C11D 1/62
                                                        8/115.51

FOREIGN PATENT DOCUMENTS

| WO | WO9859064 A1 | 12/1998 |
| WO | WO0176643 A1 | 10/2001 |
| WO | WO2007006700 A1 | 1/2007 |
| WO | WO2011120953 A1 | 10/2011 |

OTHER PUBLICATIONS

Incani, V., et al., "Lipid and hydrophobic modification of cationic carriers on route to superior gene vectors", Soft Matter, vol. 6, No. 10, Jan. 2010, pp. 2124-2138.
Philipp, A., et al., "Functional modification of amide-crosslinked oligoethylenimine for improved siRNA delivery", Reactive & Functional Polymers, Elsevier Science Publishers VV, NL, vol. 71, No. 3, Oct. 2010.
PCT/EP2013/002978 International Search Report and Written Opinion dated Nov. 29, 2013.

* cited by examiner

*Primary Examiner* — Robert M Kelly
(74) *Attorney, Agent, or Firm* — Polsinelli PC

(57) ABSTRACT

The invention provides hydroxylated polyamine derivatives, their use for the transfection of polyanions into cells, and a method of transfecting cells with a polyanion, comprising mixing said polyanion with said hydroxylated polyamine derivative in a buffer and treating said cells with the mixture obtained in the previous step.

4 Claims, 2 Drawing Sheets

Fig. 1

|   | 1 | 2 | 3 | 4 | 5 | 6 | 7 | 8 | 9 | 10 | 11 | 12 |
|---|---|---|---|---|---|---|---|---|---|----|----|----|
| A | 100 | 100 | 100 | 100 | 100 | 100 | 100 | 100 | 100 | 100 | 100 | 100 |
| B | 100 | 100 | 100 | 100 | 100 | 100 | 100 | 100 | 100 | 100 | 100 | 100 |
| C | 100 | 100 | 100 | 100 | 100 | 100 | 100 | 100 | 100 | 100 | 100 | 100 |
| D | 100 | 100 | 100 | 100 | 100 | 100 | 100 | 100 | 100 | 100 | 100 | 100 |
| E | 100 | 100 | 100 | 100 | 100 | 100 | 100 | 100 | 100 | 100 | 100 | 100 |
| F | 100 | 100 | 100 | 100 | 100 | 100 | 100 | 100 | 100 | 100 | 100 | 100 |
| G | 100 | 100 | 100 | 100 | 100 | 100 | 100 | 100 | 100 | 100 | 100 | 100 |
| H | 100 | 100 | 100 | 100 | 100 | 100 | 100 | 100 | 100 | 100 | 100 | 100 |

Fig. 2

|   | 1 | 2 | 3 | 4 | 5 | 6 | 7 | 8 | 9 | 10 | 11 | 12 |
|---|---|---|---|---|---|---|---|---|---|----|----|----|
| A | 50 | 50 | 50 | 50 | 50 | 50 | 50 | 50 | 50 | 50 | 50 | 50 |
| B | 75 | 75 | 75 | 75 | 75 | 75 | 75 | 75 | 75 | 75 | 75 | 75 |
| C | 110 | 110 | 110 | 110 | 110 | 110 | 110 | 110 | 110 | 110 | 110 | 110 |
| D | 170 | 170 | 170 | 170 | 170 | 170 | 170 | 170 | 170 | 170 | 170 | 170 |
| E | 50 | 50 | 50 | 50 | 50 | 50 | 50 | 50 | 50 | 50 | 50 | 50 |
| F | 75 | 75 | 75 | 75 | 75 | 75 | 75 | 75 | 75 | 75 | 75 | 75 |
| G | 110 | 110 | 110 | 110 | 110 | 110 | 110 | 110 | 110 | 110 | 110 | 110 |
| H | 170 | 170 | 170 | 170 | 170 | 170 | 170 | 170 | 170 | 170 | 170 | 170 |

Fig. 3

|   | 1 | 2 | 3 | 4 | 5 | 6 | 7 | 8 | 9 | 10 | 11 | 12 |
|---|---|---|---|---|---|---|---|---|---|----|----|----|
| A | 100 | 0 | 0 | 0 | 100 | 0 | 0 | 0 | 100 | 0 | 0 | 0 |
| B | 100 | 0 | 0 | 0 | 100 | 0 | 0 | 0 | 100 | 0 | 0 | 0 |
| C | 100 | 0 | 0 | 0 | 100 | 0 | 0 | 0 | 100 | 0 | 0 | 0 |
| D | 100 | 0 | 0 | 0 | 100 | 0 | 0 | 0 | 100 | 0 | 0 | 0 |
| E | 100 | 0 | 0 | 0 | 100 | 0 | 0 | 0 | 100 | 0 | 0 | 0 |
| F | 100 | 0 | 0 | 0 | 100 | 0 | 0 | 0 | 100 | 0 | 0 | 0 |
| G | 100 | 0 | 0 | 0 | 100 | 0 | 0 | 0 | 100 | 0 | 0 | 0 |
| H | 100 | 0 | 0 | 0 | 100 | 0 | 0 | 0 | 100 | 0 | 0 | 0 |

Fig. 4

|   | 1 | 2 | 3 | 4 | 5 | 6 | 7 | 8 | 9 | 10 | 11 | 12 |
|---|---|---|---|---|---|---|---|---|---|----|----|----|
| A | 50 | 0 | 0 | 0 | 50 | 0 | 0 | 0 | 50 | 0 | 0 | 0 |
| B | 75 | 0 | 0 | 0 | 75 | 0 | 0 | 0 | 75 | 0 | 0 | 0 |
| C | 110 | 0 | 0 | 0 | 110 | 0 | 0 | 0 | 110 | 0 | 0 | 0 |
| D | 170 | 0 | 0 | 0 | 170 | 0 | 0 | 0 | 170 | 0 | 0 | 0 |
| E | 50 | 0 | 0 | 0 | 50 | 0 | 0 | 0 | 50 | 0 | 0 | 0 |
| F | 75 | 0 | 0 | 0 | 75 | 0 | 0 | 0 | 75 | 0 | 0 | 0 |
| G | 110 | 0 | 0 | 0 | 110 | 0 | 0 | 0 | 110 | 0 | 0 | 0 |
| H | 170 | 0 | 0 | 0 | 170 | 0 | 0 | 0 | 170 | 0 | 0 | 0 |

HYDROXYLATED POLYAMINE DERIVATIVES AS TRANSFECTION REAGENTS

CROSS REFERENCE TO RELATED APPLICATIONS

This application is a national phase application of PCT/EP2013/002978, filed Oct. 2, 2013 which claims priority to European Patent Application No. 12006913.3, filed Oct. 5, 2012. The contents of all these applications are expressly incorporated herein by reference in their entireties.

FIELD OF THE INVENTION

The invention relates to polyamine derivatives and to the use of polyamine derivatives for the transfection of nucleic acids and other polyanions into cells. The invention also relates to a method for the transfection of polyanions into cells, and to kits and polyamine derivatives therefor. The polyamine derivatives of the invention are effective transfectants with very low toxicity that can be used for transfecting a broad range of different cell types.

STATE OF THE ART

Transfection is the introduction of foreign matter into cells. Within the context of transfection, "into cells" means transport of the foreign matter across at least one biological membrane. Further transport may occur into cellular compartments or organelles. In contrast, a mere inclusion of the material into endosomes, pinocytic or phagocytic vesicles or lysosomes is not considered a transfection.

The foreign matter may encompass molecules such as peptides, proteins and various types of nucleic acids; the latter can be as small as oligonucleotides or as long as plasmids. It may also include assemblies of such molecules. In any case, the molecules or assemblies are large and hydrophilic, two features which prevent their unassisted cellular uptake. Transfection therefore requires the use of specific helper reagents. Amongst others, polyamines can be such reagents. Polyamines form polycations in solution, which facilitates the complex formation with polyanions such as nucleic acids. These complexes are the actual transfection competent entities.

Transfection of complexes from a polyamine and a plasmid was demonstrated by Boussif et al (Proc Natl Acad Sci USA (1995), 92(16):7297-7301 or in US6013240), using branched polyethyleneimine (PEI) as the polyamine. While keeping the concept, others sought to improve the technology by various means. Strategies for improving transfectants include:

(i) selection of a specific size or configuration of the polycation, such as linear PEI of a certain length (WO2009/016507);

(ii) use of metabolically labile multimeres of such polycations (Gosselin et al. (2001) Bioconj Chem, 12(6):989-994; Lynn et al (2001) J Am Chem Soc 123(33):8155-8156; WO2007/020060 to Göpfrich et al.; WO2007/120479 to Tanaka et al.);

(iii) employment of lipid admixtures (U.S. Pat. No. 7,601,367 to Monahan et al.) or (iv) chemical modifications of the polymer backbone, e.g. grafting of aromatic amino acids (in WO2009/074970 to Adib et al.), grafting of histidine or imidazol moieties (in WO 2009/011402), alkylations as in Wakefield et al. (2005) Bioconj Chem 16(5):1204-1208 or the modification with cholesterol (in US2007/0154447 to Ferguson et al).

The hydrophobic modifications improve the membrane penetration of a transfectant (see Wakefield et al.) but are associated with a lower stability of the complex in solution; the formulated material tends to form aggregates. Grafting of polyethyleneglycol (PEG) (by Matar et al. in WO2009/021017 or in Rozema et al (2007) Proc Natl Acad Sci USA 104(32):12982-12987) counteracts aggregation but on the flip side competes with the biological activity and must be reversible as shown in the Rozema publication.

As it is evident from the many different strategies and from the large number of reports, the development of novel transfectants is a topic of intense research. Their use has substantial commercial relevance; transfection reagents had a market volume of about 200 Mio USD in 2011 (Frost & Sullivan, Global Transfection Markets, N6F0-01).

The two most important criteria in the development and improvement of transfectants are (a) a high signal-to-noise ratio and (b) efficient transfection across a large number of different cell types. The signal-to-noise ratio describes the effect of the transfection complex compared to the transfectant alone or in comparison with a transfection complex comprising an irrelevant nucleic acid.

It is therefore an objective of the invention to provide a transfectant for transfecting polyanions into cells. It is another objective to provide a transfectant that is superior to commercially available materials in the criteria (a) and/or (b). Given the large number and diversity of approaches used before, no specific rationale could be identified that would have guided such invention.

BRIEF DESCRIPTION OF THE INVENTION

The above objectives are achieved by:

(1) Use of a polyamine derivative for the transfection of polyanions into cells, said polyamine comprising:
   a polyamine moiety comprising a plurality of amino groups;
   a plurality of hydroxylated substituents comprising a hydroxyl group bonded via a hydrophobic linker to amino groups of said polyamine moiety; and
   a plurality of hydrophobic substituents bonded to amino groups of said polyamine moiety;
   said hydrophobic linker having a log P of from 2 to 20 determined for a compound obtainable from said linker by replacing bonds of said linker to the hydroxyl group and the amino group of said polyamine by bonds to hydrogen atoms; and
   said hydrophobic substituent having a log P of from 1.5 to 20 determined for a compound obtainable from said hydrophobic substituent by replacing the bond of said hydrophobic substituent to an amino group of said polyamine moiety by a bond to a hydrogen atom.

(2) Use of a polyamine derivative for the transfection of polyanions into cells, said polyamine comprising:
   a polyamine moiety comprising a plurality of amino groups;
   a plurality of hydroxylated substituents comprising a hydroxyl group bonded via a hydrophobic linker to amino groups of said polyamine moiety, wherein each of said hydroxylated substituents comprises from 4 to 40 carbon atoms, preferably from 4 to 20 carbon atoms, and more preferably from 6 to 12 carbon atoms, and each of said hydrophobic linker may comprise from 1 to 3 heteroatoms selected from O, N, and S; and a plurality of hydrophobic substituents bonded to amino groups of said polyamine moiety, wherein each of said hydrophobic substituents comprises at least 2 carbon atoms, preferably from 3 to 40 carbon atoms, and may comprise from 1 to 3 heteroatoms selected from O, N, and S provided said hydrophobic substituent has at least 6 carbon atoms.

(3) The use according to item 1 or 2, wherein each of said hydroxylated substituents of said polyamine derivative comprises any one or more of the following moieties as said hydrophobic linker: alkylene, alkenylene, alkynylene, cycloalkylene, cycloalkenylene, arylene, and combinations thereof; and/or each of said hydrophobic substituents of said polyamine derivative comprises any one or more of the following moieties: alkyl, alkenyl, alkynyl, cycloalkyl, cycloalkenyl, aryl, and combinations thereof.

(4) Polyamine derivative as defined in item 1 or 2.

(5) Polyalkylenimine derivative having one or more hydroxyalkyl substituents comprising from 4 to 40 carbon atoms, and one or more hydrophobic substituents selected from hydrocarbon substituents having at least 2 carbon atoms, preferably from 3 to 40 carbon atoms, wherein each of said hydrophobic substituents may be or may comprise an alkyl group and/or each of said hydrophobic substituents may be or may comprise an aryl group.

(6) The polyalkylenimine derivative according to item 5, wherein the hydroxyalkyl substituents and the hydrophobic substituents in said polyalkylenimine derivative have a molar ratio of from 10:1 to 0.1:1 (the C/A ratio), preferably the C/A ratio of these groups is from 3:1 to 0.33:1.

(7) The polyamine derivative or polyalkylenimine derivative according to any one of items 4 to 6, wherein said hydroxylated substituents are the same and said hydrophobic substituents are the same, and the sum of carbon atoms in one of said hydroxylated substituents plus those in one of said hydrophobic substituents is from 10 to 30, preferably from 15 to 25.

(8) Complex of a nucleic acid or a protein with the polyamine derivative of the invention.

(9) A kit comprising:
(i) a polyamine derivative as defined herein,
(ii) a buffer solution having a pH between 4 and 8, and
(iii) optionally a manual with instructions for use.

(10) A method of transfecting cells with a nucleic acid or a protein, comprising mixing said nucleic acid or a protein with a polyamine derivative as defined herein e.g. in an aqueous buffer and treating said cells with the mixture obtained in the previous step.

(11) A container comprising multiple compartments containing a lyophilized composition comprising a transfectant, said transfectant may be or may comprise the polyamine derivative as defined in any one of items 1 to 7.

The invention also provides:

(12) A use of a hydroxyalkyl-alkyl-polyamine for the transfection of polyanions into cells.

(13) The use according to item 12, wherein the polyamine moiety of said hydroxyalkyl-alkyl-polyamine is selected from the group consisting of polyalkylenimines, polyalyamines, polyvinylamines, polylysines and polyornithins, wherein said polyalkylenimines preferably are polyethylenimines, polypropylenimines, polybutylenimines or oligospermines or homologues thereof, and wherein said polyamine moiety comprises between 12 and 100000 nitrogen atoms, more preferably between 20 and 5000 nitrogen atoms.

(14) The use according to any one of items 12 or 13, wherein the hydroxyalkyl moiety is an aliphatic hydroxyalkyl moiety having between 4 and 40 carbon atoms.

(15) The use according to any one of items 12 to 14, wherein the alkyl moiety is an aliphatic alkyl moiety having at least 2 carbon atoms, preferably between 6 and 40 carbon atoms.

(16) The use according to any one of items 12 to 15, wherein all hydroxyalkyl moieties of said hydroxyalkyl-alkyl-polyamine are the same and all alkyl moieties are the same, and the sum of carbon atoms in the hydroxyalkyl moiety and the alkyl moiety is between 10 and 30, preferably between 15 and 25.

(17) The use according to any one of items 12 to 16, wherein said hydroxyalkyl-alkyl-polyamine is a linear hydroxyalkyl-alkyl-polyalkylenimine comprising structural units of the following formula (6)

wherein
x is an integer of from 1 to 10, wherein the value of x may be the same or different among different groups $(CH_2)_x$,
$R^6$ is hydrogen, $C_rH_{2r+1}$ or $C_sH_{2s}OH$,
r is an integer of from 2 to 40,
s is an integer of from 4 to 40;
or
wherein said hydroxyalkyl-alkyl-polyamine is a branched hydroxyalkyl-alkyl-polyalkylenimine comprising structural units of each of the formulae (7), (8) and (9):

wherein
$R^6$, x, r and s are as defined above and
$R^7$ comprises one or more units selected from the formulae (7), (8) and (9);
y is an integer of from 1 to 10, preferably of from 2 to 10, wherein the value of y may be the same or different among multiple occurrences of groups $(CH_2)_y$;
and wherein the number of nitrogen atoms per molecule of said linear or said branched hydroxyalkyl-alkyl-polyalkylenimine is between 12 and 100000.

(18) The use according to any one of items 12 to 17, wherein the molar ratio of hydroxyalkyl moieties to alkyl moieties in said hydroxyalkyl-alkyl-polyamine is within the range of from 6:1 to 0.33:1, preferably of from 5:1 to 1.5:1.

(19) The use according to any one of items 12 to 18, wherein at least 10 mol %, preferably between 25 and 80 mol %, more preferably between 30 and 60 mol % of amino groups of said polyamine are substituted by said hydroxyalkyl and said alkyl groups (degree of substitution).

(20) The use of according to any one of items 12 to 19, wherein the polyanions are nucleic acids.

(21) Hydroxyalkyl-alkyl-polyamine which is a branched polyethyleneimine having one or more hydroxyalkyl substituents and one or more alkyl substituents.

(22) The hydroxyalkyl-alkyl-polyamine according to item 21, wherein said hydroxyalkyl-alkyl-polyamine has one type of hydroxyalkyl moiety and one type of alkyl moiety, and the sum of carbon atoms in the type of hydroxyalkyl moiety and the type of alkyl moiety is between 10 and 30, preferably between 15 and 25.

(23) Complex of a nucleic acid with a hydroxyalkyl-alkyl-polyamine as defined in any one of the preceding items.

(24) A kit comprising:
(i) a hydroxyalkyl-alkyl-polyamine as defined in any one of items 12 to 19,
(ii) a buffer solution having a pH between 4 and 8 and an ionic strength of 0.2 mol/L or less, preferably of 0.1 mol/L or less, and
(iii) optionally a manual with instructions for use.
(25) The kit of item 24, wherein said polyamine is provided as a solution and wherein the solvent is a lower alcohol selected from the group of ethanol, propanol, 1,2-dihydroxypropane or isopropanol, or mixtures comprising water and between 33 and 100% of such lower alcohol.
(26) The kit of item 24, wherein said polyamine is provided in dry form.
(27) The kit of items 24 or 26, wherein said polyamine is provided in lyophilized form.
(28) The kit of any one of items 13 to 16, wherein said polyamine is deposited in a multi-well plate.
(29) A kit as in item 28, wherein the wells of said multi-well plate contain different amounts of said polyamine, preferably gradients of said polyamines in neighboring wells or wherein certain wells are empty.
(30) A method of transfecting cells with a polyanion, comprising mixing said polyanion with a hydroxyalkyl-alkyl-polyamine as defined in any one of items 12 to 22 in water or an aqueous buffer and treating said cells with the mixture obtained in the previous step.

Polyamines were chemically modified with hydroxylated substituents comprising a hydroxyl group bonded via a hydrophobic linker to a polyamine, and with hydrophobic substituents. The modified polyamines used in the present invention are denoted as hydroxylated, hydrophobized polyamines or as modified polyamines or as polyamine derivatives throughout this description. In one embodiment, polyamines were chemically modified with hydroxyalkyl substituents and alkyl substituents. These modified polyamines are denoted as hydroxyalkyl-alkyl-polyamines herein. It was surprisingly found that a combination of hydroxylated substituents and hydrophobic substituents on a polyamine, but not any single type of these substituents alone yields effective transfectants with a high signal-to-noise ratio. The polyamine derivatives, uses, methods, kits and hydroxyalkyl-alkyl-polyamines of the invention feature these advantageous properties on numerous cell types and are superior to commercially available transfectants and transfection methods.

DETAILED DESCRIPTION OF THE INVENTION

The polyamine derivative of this invention has hydroxylated substituents and hydrophobic substituents on a polyamine, wherein these substituents may comprise, independently from each other, one, two or three heteroatoms selected from oxygen, nitrogen or sulfur. The hydroxyalkyl-alkyl-polyamine of the invention is a polyamine derivative that has hydroxyalkyl substituents as said hydroxylated substituents and alkyl substituents as said hydrophobic substituents on a polyamine.

The polyamine derivative of the invention is obtainable by methods known in the art. One possible procedure is the derivatization of a polyamine with a halogenated hydroxy compound that forms said hydroxylated substituent upon nucleophilic substitution of the halogen by an amino group of the polyamine, and with a halogenated hydrophobic compound that forms said hydrophobic substituent upon nucleophilic substitution of the halogen by an amino group of the polyamine. The hydroxyalkyl-alkyl-polyamine of the invention is obtainable analogously. One possible procedure is the alkylation of a polyamine with a haloalkanol and with a haloalkane by nucleophilic substitution. The halo substituents of the alkanol and the alkane may be chlorine, bromine or iodine atoms, preferably they are bromine atoms. More details on the preparation of the hydroxyalkyl-alkyl-polyamine are given below.

Polyamines

The polyamine that can be used as a starting material for producing the hydroxyalkyl-alkyl-polyamine of the invention is a polymeric compound having a plurality of nitrogen atoms that form plural amino groups. These nitrogen atoms can become charged in aqueous solutions by protonation. Most aliphatic amines have a pK greater than 8 or 9 which means they are substantially or completely charged in aqueous solutions having a pH around 7.4, which is the physiological pH, or at lower pH values.

Amine moieties having a pK below 6, e.g. pyridines or anilines, are less preferred amino groups of the polyamine. The pK values of the various amines are easily available as they are frequently cited in the respective articles of the English Wikipedia found at en.wikipedia.org or they can be calculated using software, e.g. ACD/pKa database (Advanced Chemistry Development, Ontario, Canada).

The plural nitrogen atoms of the polyamines can be primary, secondary, tertiary and/or quaternary amino groups, they may also be part of ring systems. Primary, secondary, tertiary and/or quaternary amino groups may occur in the same polyamine molecule. Primary, secondary, tertiary amino groups are preferred, since they can be alkylated as described above. The polyamines may further comprise end groups (terminal groups) that may also be amino groups; however, such end groups may also be initiators or termination groups from the polymerization reaction that was used to make the polyamine.

In the case of certain linear polyamines, the internal amino groups may be secondary amino groups; examples of such polyamines are polyalkylenimines. In other linear polyamines, the amino groups are not part of the polymer backbone but of the side chain or they form the side chain by itself. In the case of branched polyamines, internal amino groups that form branching points are generally tertiary amino groups, while internal amino groups that are not branching points are generally secondary amino groups. Branches of such polymers are often terminated by primary amino groups.

In the following, the polyamines that may be used for producing the polyamine derivative of the invention are described. Thereafter, the polyamine derivative and the hydroxyalkyl-alkyl-polyamine of the invention are described.

In a first general embodiment, plural nitrogen atoms of the polyamine usable for preparing the polyamine derivative or the hydroxyalkyl-alkyl-polyamine of the invention are part of the polymeric backbone of the polyamine. The polyamine may be a linear polyamine having the plural nitrogen atoms within the polymer chain. Such polyamine may be a polyalkylenimine comprising plural units of formula (1):

$$—[CH_2—NR^1—(CH_2)_x]—, \qquad (1)$$

wherein x is an integer of from 1 to 10 and $R^1$ is hydrogen. In one embodiment, x may be an integer of from 1 to 5, preferably 1 or 2 or 3. The value of x may be the same or different among different groups $(CH_2)_x$ in the same polyamine molecule. For example, x may oscillate between two or three different values of x along the polymer chain of the polyamine, such as between values of x of 2 and 3, between values of 2 and 4, or between values 2 and 5. In the polyamines of formula (1), essentially all amino groups within the polymer chain are secondary amino groups.

If m is the number of repetitive units of formula (1) in the polyalkylenimine, m may be an integer of from 12 to 100000, preferably from 12 to 20000, more preferably from 20 to 10000, most preferably of from 20 to 5000.

Examples of polyamines that become the polyamine moiety of said polyamine derivative by nucleophilic substitution, notably by alkylation are polyalkylenimines, preferably polyethylenimines, polypropylenimines, polybutylenimines or oligospermines or homologues thereof. The polyamine moiety may comprise from 12 to 20000 nitrogen atoms, more preferably from 20 to 10000 nitrogen atoms per polyamine molecule, or as defined above for m.

Alternatively, the polyamine that may become the polyamine moiety of said polyamine derivative by nucleophilic substitution, notably by alkylation, may be a branched polyamine, preferably a branched polyalkylenimine. Such branched polyalkylenimine may be defined by having structural units of each of the following formulae (2) to (4):

  (2)

  (3)

  (4)

wherein
$R^1$ and x are as defined above;
$R^2$ comprises units of formula (2) and/or of formula (3); and
$R^3$ represents hydrogen.

In the branched polyalkylenimine, a main chain thereof may be formed by the divalent units of formula (2) comprising secondary amino groups. However, the branched polyalkylenimine, notably a main chain thereof, comprises at least 1 divalent unit of formula (3) that comprises the tertiary nitrogen bound to $R^2$ as a branching point. Branching polymer chains comprise at least one, generally multiple, unit(s) of formula (2), and may further comprise one or more units of formula (3), leading to further branching. Thus, the branched polyalkylenimine may be a dendrimer or a dendronized polymer. In many cases these branched polyalkylenimines comprise the structural elements (2), (3) and (4) in a random sequence leading to irregular structures or random polyamines. The monovalent group of formula (4) defines end groups of the polyalkylenimine that may be present on a main chain as well as on branch chains. Multiple structures of each of formulae (2), (3) and (4) present in the polyalkylenimine may be the same or different in terms of x, $R^2$ and $R^3$.

The degree of branching in the branched polyalkylenimine may be from 1 to 40%, preferably of from 10 to 40%, more preferably of from 15 to 30%. The skilled artisan knows how to quantify the branching of a polymer, e.g. through pH-titrations and quantification of the different compartments of the titration curve or by 1H NMR measurements.

A measure for the degree of branching in a branched polyalkylenimine is the proportion of primary, secondary and tertiary amino groups. While a linear polyalkylenimine has exclusively secondary amino groups as internal amino groups, branched polyalkylenimines have tertiary amino groups such as of formula (3), the amount of which increases with increasing degree of branching. The molar proportion of primary amino groups in the branched polyamine may be from 1 to 40%, preferably from 15 to 30%. The molar proportion of secondary amino groups may be from 15 to 85%, preferably from 30 to 70%. The molar proportion of tertiary amino groups may be from 1 to 40%, preferably from 15 to 30%.

Examples of branched polyamines that may become the polyamine moiety of said polyamine derivative or said hydroxyalkyl-alkyl-polyamine are branched polyalkylenimines, preferably branched polyethylenimines, branched polypropylenimines, or branched polybutylenimines. The branched polyamines, such as the branched polyalkylenimines, may have between 12 and 100000 nitrogen atoms, more preferably between 20 and 20000 nitrogen atoms per polyamine molecule. In other embodiments, the number of nitrogen atoms in such polymers is between 20 and 5000 nitrogen atoms per molecule of polyamine.

Examples of polyamines having a charged backbone in aqueous medium at neutral pH for use for producing the polyamine derivative or the hydroxyalkyl-alkyl-polyamine of the invention are listed in the table 1 below:

TABLE 1

| Polymer | x | number of nitrogen atoms | remarks |
| --- | --- | --- | --- |
| linear polyethylenimine | 1 | 45-75 | Mr 2 . . . 3.1 kDa |
| linear polyethylenimine | 1 | 450-750 | Mr 20 . . . 31 kDa |
| linear polyethylenimine | 1 | 1850-2900 | Mr 80 . . . 125 kDa |
| linear polyethylenimine | 1 | 4500-7500 | Mr 200 . . . 310 kDa |
| branched polyethylenimine | 1 | 12-17 | Mr 480 . .. 750 Da |
| branched polyethylenimine | 1 | 23-35 | Mr 960 . . . 1500 Da |
| branched polyethylenimine | 1 | 33-52 | Mr 1440 . . . 2250 Da |
| branched polyethylenimine | 1 | 185-290 | Mr 8 . . . 12.5 kDa |
| branched polyethylenimine | 1 | 1300-2000 | Mr 56 . . . 87 kDa |
| branched polyethylenimine | 1 | 14000-22000 | Mr 600 . . . 950 kDa |
| branched polyethylenimine | 1 | 37000-58000 | Mr 1.6 . . . 2.5 MDa |
| polybutylenimine | 2 | 20-50 | |
| | 2 | 50-200 | |
| | 2 | 200-500 | |
| | 2 | 500-2000 | |
| oligospermine | 2, 3 alternating | 12-24 | |
| | 2, 3 alternating | 20-32 | |
| | 2, 3 alternating | 28-48 | |
| oligo(C3, C5)spermine | 2, 4 alternating | 12-24 | |
| | 2, 4 alternating | 20-32 | |
| | 2, 4 alternating | 28-48 | |
| oligo(C3, C6)spermine | 2, 5 alternating | 12-24 | |
| | 2, 5 alternating | 20-32 | |
| | 2, 5 alternating | 28-48 | |

In table 1, Mr means relative molecular weight in terms of the number average molecular weight (Mn).

Another example of a branched polyamine is the polyethylenime of the following structure:

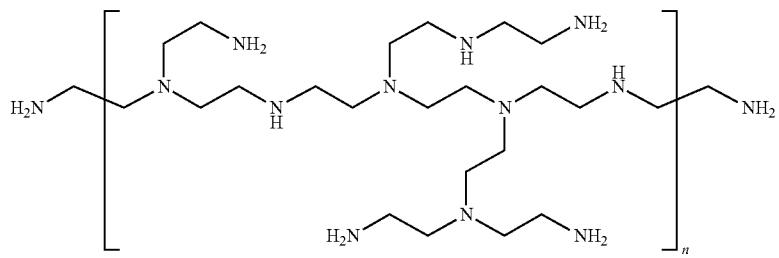

n being an integer such that the number average molecular weight Mn is about 10 000 and having a CAS number 9002-98-6. It is available commercially from Sigma-Aldrich, catalog no. 408727. Yet other branched polyamines are listed in the examples.

Polyamines may also form multimeric assemblies of polyamine oligomers. An example for a branched polyamine is branched polyethylenimine. Examples for the multimeric assemblies were described in Gosselin et al. (2001) Bioconj Chem, 12(6):989-994; Lynn et al (2001) J Am Chem Soc 123(33):8155-8156; WO2007/020060 to Göpfrich et al. or WO2007/120479 to Tanaka et al.

In a second general embodiment, the charged nitrogen atoms of the polyamine usable for producing the polyamine derivative or the hydroxyalkyl-alkyl-polyamine of the invention are not part of the polymer backbone but are present in side chains of the polyamine. In some embodiments, the polyamine may be a derivatives of polyethylene, such as polyallylamine, polyvinylamine, cationized polyacrylate or a polyvinylether of structure (5),

$$—[CH_2—CHR^4]_p—, \quad (5)$$

wherein
$R^4$ is selected from $—NH_2$, $—CH_2—NH_2$, $—O—CH_2—CH_2—NH_2$ or $—C(=O)O—R^5$, wherein
$R^5$ is selected from $—CH_2—CH_2—NH_2$, $—CH_2—CH_2—NH—CH_3$, $—CH_2—CH_2—N—(CH_3)_2$, and $—CH_2—CH_2—N—(CH_2—CH_3)_2$.

The variable p is an integer that indicates the size of the polymer and may vary between 20 to about 50000. In preferred embodiments, p is between 20 and 5000, in more preferred embodiments p is between 100 and 2000.

In other embodiments, the polymers are polypeptides such as polylysines, polyornithins, polyarginines and the like. The number amino acid residues in these polypeptides may be as defined above for p. In yet other embodiments, the polymer may have a sugar backbone such as chitosan.

As with the first general embodiment, the polymers of the second general embodiment may also be of linear, branched or of dendrimer type, they may also be multimeric assemblies of polyamine oligomers.

Examples of polyamines having charged side-chains for the second general embodiment are listed in the Table 2 below:

TABLE 2

| Polymer | $R^4$ | $R^5$ | p |
|---|---|---|---|
| Poly-allylamine | $CH_2—NH_2$ | — | 2000 . . . 3300 |
| Poly-allylamine | $CH_2—NH_2$ | — | 200-330 |
| Poly-vinylamine | $NH_2$ | — | 450 . . . 750 |
| Poly-N-methylvinylamine | $NH—CH_3$ | — | 2000 . . . 3300 |

TABLE 2-continued

| Polymer | $R^4$ | $R^5$ | p |
|---|---|---|---|
| Poly-(2-(N,N-dimethylamino)ethyl acrylate) | $C(=O)O—R^5$ | $CH_2—CH_2—N—(CH_2—CH_3)_2$ | 280 . . . 450 |

For achieving high performance in transfection, a polyamine such as those described above is modified both with hydroxyl and hydrophobic moieties for obtaining the polyamine derivative of the invention.

Hydroxylated Substituents

The hydroxylated substituents comprise a hydroxy group bonded via a hydrophobic linker to amino groups of the polyamine, said hydrophobic linker may have a partition coefficient log P of between 2 and 20, preferably between 2 and 10, and more preferably between 3 and 6, determined for a compound obtainable from said linker by replacing bonds of said linker to the hydroxy group and the amino group of the polyamine by bonds to hydrogen atoms. Methods to determine the log P are known to the skilled artisan and comprise the experimental determination of the compound distribution between water and 1-octanol, or obtaining such values from reference sources such as Wikipedia, the English version, or calculating the log P using software such as ACD/Labs 7.0 (Advanced Chemistry Development, Ontario, Canada).

A hydroxylated substituent may comprise one or two hydroxy groups, preferably one hydroxy group. The hydroxylated substituents are moieties comprising at least 4 carbon atoms. In some aspects of the invention, the hydroxylated substituents have from 4 to 40 carbon atoms, preferably from 6 to 20, more preferably from 6 to 12 carbon atoms. In a preferred aspect, the hydroxylated substituents are linear structures having from 4 to 20 carbon atoms, preferably between 6 and 12.

The hydrophobic linkers of said hydroxylated substituents may comprise from 1 to 3, preferably 1 or 2, heteroatoms selected from O, N, and S. Preferably, the heteroatoms are selected from O and S. In one embodiment, 1 or 2 heteroatoms selected from O, N and S, preferably O and S, may be contained in the hydrophobic linker. Thus, the hydroxylated substituents may be hydroxyhydrocarbyl groups, or they may be hydroxyheterohydrocarbyl groups comprising from 1 to 3 heteroatoms selected from O, N, and S, preferably selected from O and S. Among the plurality of hydroxylated substituents of a molecule of said polyamine derivative, there may be exclusively hydroxyhydrocarbyl groups, exclusively hydroxyheterohydrocarbyl groups, or there may be hydroxyhydrocarbyl groups and hydroxyheterohydrocarbyl groups.

Where the hydroxylated substituents are hydroxyhydrocarbyl groups, the hydrocarbyl moieties thereof may be saturated aliphatic hydrocarbyl moieties, unsaturated aliphatic hydrocarbyl moieties, alicyclic hydrocarbyl moieties, aromatic hydrocarbyl moieties, or moieties comprising two or more moieties from the aforementioned list.

Examples of the hydroxyhydrocarbyl groups are hydroxyalkyl groups, hydroxyalkenyl groups, hydroxyalkynyl groups, hydroxycycloalkyl groups, hydroxycycloalkenyl groups, hydroxyalkylcycloalkyl groups, hydroxycycloalkylalkyl groups, hydroxyalkylcycloalkylalkyl groups, hydroxyaryl groups, hydroxyalkylaryl groups, hydroxyarylalkyl group, and hydroxyalkylarylalkyl groups. Examples and definitions of the hydrocarbyl groups to which the hydroxy group is bound are also given below in the context of the hydrophobic substituents. Multiple different such hydrocarbyl groups may be combined. However, the log P values and/or the carbon atom number definitions given above apply.

It is possible to replace 1, 2 or 3, preferably 1 or 2, of the carbon atoms of the hydrocarbyl moieties of the hydroxylated substituents by oxygen, nitrogen or sulfur, thereby forming the hydroxyheterohydrocarbyl moieties. It is understood that any such formal replacement by a heteroatom will include adjustment of bound hydrogen atoms to adjust to the valency of the exchanged heteroatom. In preferred embodiments, such hydroxyheterohydrocarbyl moieties comprise one or more functional group selected from —O—, —S—, —N(H)C(O)—, —C(O)O—, —OC(O)N(H)—, —C(O)—, —C(O)—N(H)—, —N(H)—C(O)—O—, —O—C(O)—, or —S—S— in the hydrophobic linker.

In one aspect of the invention, the hydrophobic linkers are or comprise alkylene groups such as linear or branched alkylene groups, or the linkers are or comprise cycloalkylene groups. Alkylene groups may be n-alkylene or isoalkylene groups. Examples of alkylene groups are propylene, butylene, pentylene, hexylene, heptylene, octylene, nonylene, decylene, undecylene, dodecylene, tetradecylene or hexadecylene groups. Examples of cycloalkylene groups are cyclopentylene, cyclohexylene and cycloheptylene groups. Examples of alkylcycloalkyl groups are methylcyclopentylene, ethylcyclopentylene, propylcyclopentylene, butylcyclopentylene, pentylcyclopentylene, hexylcylopentylene, methylcyclohexylene, ethylcyclohexylene, propylcyclohexylene, butylcyclohexylene, pentylcyclohexylene and hexylcylohexylene. One or more of these may be combined in a hydrophobic linker.

The hydroxylated substituents may be or may comprise hydroxyalkyl or hydroxycycloalkyl groups and comprise between 4 and 20, preferably, between 6 and 12 carbon atoms. Such hydroxylated substituents may be selected from the group consisting of hydroxy-n-alkyl groups, branched hydroxyalkyl groups or cyclic hydroxyalkyl groups and their constitution or conformation isomers. In a preferred embodiment, the hydroxyalkyl groups are radicals of alcohols selected from butanol, pentanol, hexanol, heptanol, octanol, nonanol, decanol, undecanol, dodecanol, tetradecanol, hexadecanol, 2-cyclohexylethanol, 4-cyclohexylbutanol, 6-cyclohexylhexanol, 2-(2', 3' or 4' ethylcyclohexyl)-ethanol or 4-(2', 3' or 4' ethylcyclohexyl)-butanol or 6-(2', 3' or 4' ethylcyclohexyl)-hexanol.

In another aspect, the hydrophobic linkers are or comprise arylene groups and have between 6 and 20, preferably between 6 and 12 carbon atoms. Aryl groups forming said arylene groups include aromatic hydrocarbyl groups (carbon-only aryl groups) and aromatic heterohydrocarbyl groups (heteroaryl groups). Examples of the former are phenyl, naphthyl, anthracenyl and phenanthryl. Nitrogen-containing heteroaryl groups preferably shall have a pK value of <5 for avoiding additional cationic charges at neutral pH. Examples of such nitrogen-containing heteroaryl groups are indolyl groups, pyrazinyl groups, pyridazinyl groups, pyrimidinyl groups, cinnolinyl groups, phthalazinyl groups and purinyl groups.

Examples of alkylaryl groups are methylphenyl (tolyl), ethylphenyl, 4-isopropylphenyl, and xylyl groups. Examples of arylalkyl (aralkyl) groups are benzyl, phenylethyl and trityl groups. Examples of alkylarylalkyl groups are methylbenzyl and 4-isopropylbenzyl groups.

Hydroxyarylalkyl moieties may for example be radicals derived from o-, m- or p-cresol or o-, m- or p-ethyl phenol or alkyl homologues thereof. Hydroxyalkylarylalkyl moieties may for example be 2-(o-, m- or p-methyl phenyl) ethanol.

Multiple hydroxylated substituents present on the polyamine derivative of the invention may be the same or different. For simplicity, they may be the same. The hydroxy group of the hydroxylated substituent may be bound to any carbon atom of the hydrophobic linker. Preferably, the hydroxyl group is bound to a carbon atom as follows: if z is the number of carbon atoms in the longest carbon chain in the hydroxylated substituent (such as the hydroxyalkyl group) to the carbon atom that is bound to a polyamine nitrogen atom, the hydroxyl group is bound to a carbon atom at a position that is more than z/2 positions away from the polyamine nitrogen, if the carbon atom bound to the polyamine nitrogen is counted as position 1. If the value of z/2 is not an integer, the above definition leads to the position defined by the next integer >z/2. In one embodiment, the hydroxyl group is bound to the carbon atom of the hydrophobic linker that is most remote (in terms of the number of carbon atoms) from the polyamine nitrogen atom to which the hydrophobic linker (an alkylene chain in the case of hydroxyalkyl groups) is connected. The hydroxy group may be bound to the carbon atom that is farthest away from the polyamine nitrogen within the hydroxylated substituent (or hydroxyalkyl group), such as to the terminal (omega position) carbon atom of said substituent (in case of a linear hydroxylated substituent).

The possible groups given above for the hydrophobic linkers may be substituted provided the log P values given above are fulfilled. Alternatively, the possible groups given above for the hydrophobic linkers may be substituted provided the carbon atom numbers and numbers of possible heteroatoms as defined above are fulfilled.

Hydrophobic Substituents

The hydrophobic substituents may be bonded to amino groups of the polyamine and may have a log P of from 1.5 to 20, preferably of from 2 to 15, more preferably of from 2.5 to 10, determined for a compound obtainable from said hydrophobic substituent by replacing its bond to an amino group of the polyamine by a bond to a hydrogen atom. Methods to determine the log P are known to the skilled artisan and comprise the experimental determination of the compound distribution between water and 1-octanol phases, or obtaining such values from reference sources such as Wikipedia, the English version, or calculating the log P using software such as ACD/Labs 7.0 (Advanced Chemistry Development, Ontario, Canada).

The hydrophobic substituents comprise at least 2 carbon atoms. In some aspects of the invention, the hydrophobic substituents have between 3 and 40 carbon atoms, preferably from 6 to 20 carbon atoms. In preferred aspects, the hydrophobic substituents are linear alkyl groups having between 6 and 40 carbon atoms, in more preferred aspects the number of carbon atoms is between 6 and 20.

The hydrophobic substituents may comprise from 1 to 3, preferably 1 or 2, heteroatoms selected from O, N, and S, provided said hydrophobic substituents comprise 6 or more carbon atoms. Preferably, the heteroatoms are selected from O and S. Thus, the hydrophobic substituents may be hydrocarbyl groups or heterohydrocarbyl groups, the latter comprising from 1 to 3 heteroatoms as mentioned before. Among the plurality of hydrophobic substituents of a molecule of said polyamine derivative, there may be exclusively hydrocarbyl groups, exclusively heterohydrocarbyl groups, or there may be hydrocarbyl groups and heterohydrocarbyl groups. In one embodiment, the plurality of hydrophobic substituents are all hydrocarbyl groups. In another embodiment, the plurality of hydrophobic substituents are all heterohydrocarbyl groups.

Where the hydrophobic substituents are hydrocarbyl groups, they may be selected from alkyl groups, alkenyl groups, alkynyl groups, cycloalkyl groups, cycloalkenyl groups, cycloalkylalkyl groups, alkylcycloalkyl groups, alkylcycloalkylalkyl groups, aryl groups, alkylaryl groups, arylalkyl groups, and alkylarylalkyl groups and groups comprising two or more groups from the aforementioned list. Provided the hydrophobic substituent comprises 6 or more carbon atoms, it is possible to replace 1, 2 or 3 of the carbon atoms of said hydrocarbyl groups by oxygen, nitrogen or sulfur, preferably oxygen or sulfur, thereby forming heterohydrocarbyl substituents. Such heterohydrocarbyl substituents may comprise functional groups selected from —O—, —S—, —N(H)C(O)—, —C(O)O—, —OC(O)N(H)—, —C(O)—, —C(O)—N(H)—, —N(H)—C(O)—O—, —O—C(O)—, or —S—S—.

In one aspect of the invention, the hydrophobic substituents are or comprise alkyl groups such as linear or branched alkyl groups, or cycloalkyl groups. Alkyl groups may be n-alkyl or isoalkyl groups. Examples of alkyl groups are propyl, butyl, pentyl, hexyl, heptyl, octyl, nonyl, decyl, undecyl, dodecyl, tetradecyl or hexadecyl groups. Examples of cycloalkyl groups are cyclopentyl, cyclohexyl and cycloheptyl groups.

Examples of alkenyl groups are propenyl, butenyl, pentenyl, hexenyl, heptenyl, octenyl, nonenyl, decenyl, undecenyl, dodecenyl, tetradecenyl and hexadecenyl groups. Examples of alkynyl groups are propynyl, butynyl, pentynyl, hexynyl, heptynyl, octynyl, nonynyl, decynyl, undecynyl, dodecynyl, tetradecynyl and hexadecynyl groups.

Examples of cycloalkenyl groups cyclopentenyl, cyclohexenyl and cycloheptenyl groups.

Cycloalkylalkyl groups are groups wherein a cycloalkyl group is linked to an alkylene group corresponding to an alkyl group. Examples are cyclopentylmethyl, cyclopentylethyl, cyclohexylmethyl, cyclohexylethyl etc.

Alkylcycloalkyl groups are groups wherein an alkyl group is linked to a cycloalkylene group corresponding to a cycloalkyl group. Examples of alkylcycloalkyl groups are methylcyclopentyl, ethylcyclopentyl, propylcyclopentyl, butylcyclopentyl, pentylcyclopentyl, hexylcyclopentyl, methylcyclohexyl, ethylcyclohexyl, propylcyclohexyl, butylcyclohexyl, pentylcyclohexyl and hexylcylohexyl.

Alkylcycloalkylalkyl groups are groups wherein an alkyl group is linked to a cycloalkylalkylene group.

In another aspect of the invention, the hydrophobic substituent comprises an aryl groups and has between 6 and 20 carbon atoms. Aryl groups include aromatic hydrocarbyl groups (carbon-only aryl groups) and aromatic heterohydrocarbyl groups (heteroaryl groups). Examples of the former are phenyl, naphthyl and phenanthryl. Nitrogen-containing heteroaryl groups preferably have a pK value of <5 for avoiding additional cationic charges at neutral pH. Examples of such nitrogen-containing heteroaryl groups are indolyl groups pyrazinyl groups, pyridazinyl groups, pyrimidinyl groups, cinnolinyl groups, phthalazinyl groups and purinyl groups. Oxygen-containing heterohydrocarbyl groups that form hydroxy groups preferably have a pK>12 for avoiding negative charges at neutral pH.

Examples of alkylaryl groups are methylphenyl (tolyl), ethylphenyl, 4-isopropylphenyl, methylindolyl and xylyl groups. Examples of arylalkyl (aralkyl) groups are benzyl, phenylethyl, indolylmethyl and trityl groups. Examples of alkylarylalkyl groups are methylbenzyl and 4-isopropylbenzyl groups.

Polyamine Derivatives

The polyamine derivative of the invention may be a linear polyalkylenimine derivative comprising units of the following formula (10):

$$—[CH_2—NR^{10}—(CH_2)_x]— \quad (10)$$

wherein x is an integer of from 1 to 10, wherein the value of x may be the same or different among different groups $(CH_2)_x$, $R^{10}$ is hydrogen, the hydroxylated substituent comprising a hydroxyl group bonded via a hydrophobic linker (as defined above) to the amino nitrogen to which $R^{10}$ is bonded, or the hydrophobic substituent as defined above, each of which is present in a molecule of said polyalkylenimine among different occurrences of $R^{10}$.

The number of nitrogen atoms per molecule of said linear polyalkylenimine or another polyamine moiety of the polyamine derivative may be from 12 to 100000, preferably from 12 to 20000, more preferably from 20 to 10000, and most preferably of from 20 to 5000. Multiple occurrences of $R^{10}$ may be the same of different.

The linear polyamine derivative that was defined above by way of the repeating units of the polymer chain has terminal groups that are generally as formed in the production of the underlying polyamine. Thus, there are no limitations in the invention regarding the end groups. In the case of linear polyethylenimines, there may be hydroxyethyl end groups. Examples for end groups are those of $R^8$ defined below.

Alternatively, the polyamine derivative of the invention is a branched polyalkylenimine derivative comprising units of each of the formulae (11), (12) and (13):

$$—[CH_2—NR^{10}—(CH_2)_x]— \quad (11)$$

$$—[CH_2—NR^{11}—(CH_2)_x]— \quad (12)$$

and $$—(CH_2)_y—NR^{10}_2 \quad (13)$$

wherein $R^{10}$ and x are as defined above;

$R^{11}$ comprises one or more units selected from formulae (11), (12) and (13);

y is an integer of from 1 to 10, wherein the value of y may be the same or different among different groups $(CH_2)_y$; and wherein the number of nitrogen atoms per molecule of said linear or said branched polyalkylenimine is between 12 and 100000.

The number of nitrogen atoms per molecule of said branched polyalkylenimine derivative may be as defined above for the linear polyalkylenimine. Examples for end groups are those of $R^8$ defined below. The degree of branching in the branched polyalkylenimine may be of from 1 to 40%, preferably from 10 to 40%, more preferably from 15 to 30%. The skilled artisan knows how to quantify the branching of a polymer, e.g. through pH-titrations and quantification of the different compartments of the titration curve or by 1H-NMR analysis.

Combinations of hydroxylated substituents and hydrophobic substituents in the polyamine derivatives can be characterized by their molar ratio. It was found that the polyamine derivatives (such as polyethylenimine derivatives) of the invention perform best if the hydroxylated substituents and hydrophobic substituents have a molar ratio of from 10:1 to 0.1:1 (the O/A ratio). In a preferred embodiment, the O/A ratio of these groups is from 3:1 to 0.33:1.

When grafted onto a polyamine, the degree of substitution (DOS) is another feature of relevance. The DOS is defined as the molar percentage of the sum of hydroxylated substituents and hydrophobic substituents per amino group of the polyamine. The DOS is least 10%, preferably from 25 to 80%, more preferably from 30 to 60%. A person skilled in the art knows how to determine the DOS of a polyamine derivative. This can be achieved by measurement of the residual nitrogen atoms on a polymer for example using the ninhydrin reaction. Another possibility is the use of 1H-NMR spectroscopy.

In some aspects, the invention is practiced with a combination of one specific type of said hydroxylated substituent and one specific type of said hydrophobic substituents per molecule of polyamine derivative. In such aspects, the sum of carbon atoms of one hydroxylated substituent plus that in one hydrophobic substituent is from 10 to 30, preferably this sum is from 15 to 25.

In further aspects, specific combinations are made between a polyamine type, polyamine molecular mass, size of the hydroxylated substituent and size of the hydrophobic substituent.

In preferred embodiments, the polyamine derivative has a linear polyethylenimine moiety of from 50 to 500 kDa (in terms of number average molecular weight), the hydroxylated substituent is a hydroxyalkyl group having from 6 to 12 carbon atoms and the hydrophobic substituent is a hydrocarbyl moiety having from 3 to 12 carbon atoms and is selected from n-alkyls, cyclic alkyls, preferably from cycloalkyls such as the cyclohexyl moiety, or from aryls, preferably from aryl-containing groups such as a phenylalkyl or alkylphenylalkyl group.

In other preferred embodiments, the polyamine derivative has a branched polyethylenimine moiety of from 0.5 to 2.5 kDa (in terms of number average molecular weight), the hydroxylated substituent is a hydroxyalkyl group having from 6 to 12 carbon atoms and the hydrophobic substituent is a hydrocarbyl moiety having from 3 to 12 carbon atoms and is selected from n-alkyls or from aryls, preferably from aryl-containing groups such as phenylalkyl or alkylphenylalkyl.

In yet other preferred embodiments, the polyamine derivative has a branched polyethylenimine moiety of from 50 to 100 kDa (in terms of number average molecular weight), the hydroxylated substituent is a hydroxyalkyl group having from 6 to 12 carbon atoms and the hydrophobic substituent is a hydrocarbyl moiety having from 3 to 12 carbon atoms and may be selected from n-alkyls.

In still other preferred embodiments, the polyamine derivative has a branched polyethylenimine moiety of from 50 to 100 kDa (in terms of number average molecular weight), the hydroxylated substituent is a hydroxyalkyl group having about 4 carbon atoms, and the hydrophobic substituent is a hydrocarbyl moiety having from 3 to 12 carbon atoms and contains an aryl group, preferably from aryl comprising a phenylalkyl or alkylphenylalkyl moiety.

Hydroxyalkyl-alkyl-poylamines

The hydroxyalkyl-alkyl-polyamine of the invention may be a linear hydroxyalkyl-alkyl-polyalkylenimine comprising, or consisting essentially of, units of the formula (6):

$$—[CH_2—NR^6—(CH_2)_x]— \qquad (6),$$

wherein x is an integer of from 1 to 10, and wherein the value of x may be the same or different among different groups $(CH_2)_x$; $R^6$ is hydrogen, an alkyl group of formula $C_rH_{2r+1}$ or a hydroxyalkyl group of formula $C_sH_{2s}OH$. Each of these groups of $R^6$ is present in a molecule of said hydroxyalkyl-alkyl-polyamine among different occurrences of $R^6$; r is an integer of from 2 to 40, and s is an integer of from 4 to 40. Preferred embodiments for x are as defined above in the context of formula (1). Numeral r is preferably of from 4 to 20, more preferably from 6 to 12. Numeral s is preferably from 3 to 40, more preferably from 5 to 20, and even more preferably from 6 to 12.

The number of nitrogen atoms per molecule of said linear hydroxyalkyl-alkyl-polyalkylenimine may be from 12 to 100000, preferably from 12 to 20000, more preferably from 20 to 10000, even more preferably of from 50 to 5000, and most preferably of from 200 to 2000.

The linear hydroxyalkyl-alkyl-polyamine that was defined above by way of the repeating units of the polymer chain has terminal groups that are generally as formed in the production of the underlying polyamine. Thus, there are no limitations in the invention regarding the end groups. Examples for end groups are those of $R^8$ defined below.

Alternatively, said hydroxyalkyl-alkyl-polyamine is a branched hydroxyalkyl-alkyl-polyalkylenimine. The branched hydroxyalkyl-alkyl-polyalkylenimine may be one comprising structural units of each of the formulae (7), (8) and (9):

$$—[CH_2—NR^6—(CH_2)_x]— \qquad (7)$$

$$—[CH_2—NR^7—(CH_2)_x]— \qquad (8)$$

$$—CH_2—NR^6_2 \qquad (9)$$

wherein
$R^6$, x, r and s are as defined above;
$R^7$ comprises one or more structures selected from formulae (7), (8) and (9);
y is an integer of from 1 to 10, preferably of from 2 to 10, more preferably of from 2 to 6, wherein the value of y may be the same or different among different occurrences of groups $(CH_2)_y$.

$R^7$ may be a group of formula (9) or $R^7$ comprises one or more units of formula (7) and/or (8). It is also possible that $R^7$ comprises one or more units of formula (7) and one or more units of formula (8). As the hydroxyalkyl-alkyl-polyalkylenimine is polymeric, one molecule thereof generally comprises multiple groups $R^7$ that differ in structure.

The number of nitrogen atoms per molecule of said branched hydroxyalkyl-alkyl-polyalkylenimine is from 12 to 100000, preferably from 20 to 20000, more preferably from 20 to 10000, even more preferably of from 20 to 5000, and most preferably from 100 to 2000.

The degree of branching in the branched polyalkylenimine may be of from 1 to 40%, preferably from 10 to 40%, more preferably from 15 to 30%. The skilled artisan knows how to quantify the branching of a polymer, e.g. through pH-titrations and quantification of the different compartments of the titration curve.

Molar ratios of hydroxyalkyl and alkyl groups in the above-described hydroxyalkyl-alkyl-polyalkylenimine may be as defined below. The degree of substitution (DOS) may also be as defined below.

In some aspects, the invention is practiced with specific combinations of hydroxyalkyl and alkyl moieties, each of which is generally present multiple times on the hydroxyalkyl-alkyl-polyamine. In a preferred embodiment, one type of hydroxyalkyl group is combined with one type of alkyl group and the sum of carbon atoms in both moieties is between 10 and 30, in more preferred embodiments this sum is between 15 and 25.

In further aspects, specific combinations are made between a polyamine type, polyamine molecular mass, length of the hydroxyalkyl moiety and length of the alkyl moiety. In one embodiment, the polyamine is a linear polyethylenimine of between 2 and 30 kDa (in terms of number average molecular weight), the hydroxyalkyl group has between 5 and 9 carbon atoms and the alkyl group has between 6 and 16 carbon atoms.

In another embodiment, the polyethylenimine is a branched polymer of about 10 kDa (Mn) and the hydroxyalkyl group has about 9 carbon atoms and the alkyl group has about 12 carbon atoms.

Combinations of hydroxyalkyl and alkyl groups in the hydroxyalkyl-alkyl-polyamine can be characterized by their molar ratio. It was found that the hydroxyalkyl-alkyl-polyamines (such as the hydroxyalkyl-alkyl-polyethylenimines) of the invention perform best if the hydroxyalkyl and alkyl moieties have a molar ratio between 6:1 and 0.33:1 (the O/A ratio). In preferred embodiments, the O/A ratio of these groups is between 5:1 and 0.8:1. More preferred is an O/A ratio between 5:1 and 1.5:1.

When grafted onto a polymer, the degree of substitution (DOS) is another feature of interest. The DOS is defined as the molar percentage of the sum of hydroxyalkyl moieties and alkyl moieties per amino group of the polyamine. The DOS is least 10%, preferably between 25 and 80%, more preferably between 30 and 60%. A person skilled in the art knows how to determine the DOS of a polyamine derivative. This can be achieved by measurement of the residual nitrogen atoms on a polymer for example using the ninhydrin reaction. Another possibility is the use of 1H-NMR spectroscopy.

The following table 3 lists possible embodiments of modified polyamines. For a list of the abbreviations of chemical names, see examples 11 and 15.

TABLE 3

| Polymer | Mr of the polyamine in kDa | hydroxyl moiety | hydrophobic moiety | O/A ratio | DOS |
|---|---|---|---|---|---|
| Modified polyamines for the transfection of oligonucleotides | | | | | |
| Linear Polyethylenimine | 2.5 kDa | O6-O10 | A3-A12 | 0.8-4 | 40-60% |
| Linear Polyethylenimine | 25 kDa | O4-O6 | A6-A12 | 1.5-4 | 50-70% |
| Branched Polyethylenimine | 10 kDa | O6-O10 | A3-A12 | 1.5-5 | 30-70% |
| Branched Polyethylenimine | 10 kDa | O9 | A6-A12 | 1.5-5 | 35-55% |
| Branched polyethylenimine | 1.2 kDa | O6 | BB or 2-BEB | 0.5-2 | 40-60% |
| Branched polyethylenimine | 1.2 kDa | O9 | A3 | 2-10 | 40-60% |
| Branched polyethylenimine | 70 kDa | O6 . . . O9 | A3 . . . A9 | 0.75-6 | 40-60%, 20 . . . 40% for the combination of O9 and A9 |
| Branched polyethylenimine | 70 kDa | O4 | BB or 4-IPBB | 0.5-3 | 40-60% |
| Linear polyethylenimine | 250 kDa | O6 . . . O9 | A3 . . . A9 | 1-10 | 20 . . . 50%; 40 . . . 60% for combinations of O6 and A6 |
| Linear polyethylenimine | 250 kDa | O9 | BB, 2-BEB, 4-IPBB | 0.5-3 | 40-60% |
| Linear polyethylenimine | 250 kDa | O9 | B2CHE | 0.5-3 | 40-60% |
| Modified polyamines for the transfection of plasmids | | | | | |
| Branched polyethylenimine | 1.2 kDa | O4 . . . O12 | A12 | 0.1-1 | 40-60% |
| Branched polyethylenimine | 1.2 kDa | O6 | BB or 4-IPBB | 0.1-1 | 40-60% |
| Branched polyethylenimine | 70 kDa | O6 . . . O12 | A9 . . . A12 | 0.1-1 | 40-60%; 20-50% in for combinations of O6 and A12 |
| Branched polyethylenimine | 70 kDa | O4 . . . O12 | BB or 4-IPBB | 0.1-1 | 15-60% |
| Linear polyethylenimine | 250 kDa | O9 | A3-A12 | 0.5-10 | 20-50% |

TABLE 3-continued

| Polymer | Mr of the polyamine in kDa | hydroxyl moiety | hydrophobic moiety | O/A ratio | DOS |
|---|---|---|---|---|---|
| Linear polyethylenimine | 250 kDa | O4-O12 | BB, 2BEB, 4-IPBB | 0.5-3 | 15-60% |
| Linear polyethylenimine | 250 kDa | O4 ... O12 | B2CHE | 0.1-3 | 15-60% |
| Modified polyamines based on oligospermines | | | | | |
| x = 2, 3 | 1-4 kDa | O9 ... O12 | Ethyl | 0.2-1 | 50-100% |
| x = 2, 4 | 2-6 kDa | O12 | Ethyl | 0.2-1 | 50-100% |
| x = 2, 5 | 1-4 kDa | O9 ... O12 | Ethyl | 0.2-1 | 50-100% |
| x = 2, 4 | 1-6 kDa | O9 | Butyl | 0.2-1 | 50-100% |
| x = 2, 3 | 2-6 kDa | O9 | Hexyl | 0.2-1 | 50-100% |
| x = 2, 4 | 1-6 kDa | O9 ... O12 | Hexyl | 0.2-1 | 50-100% |

Manufacture of Polyamine Derivatives

The polyamine derivatives or the hydroxyalkyl-alkyl-polyamine of the invention may be prepared by modification of any of the polyamines described above with the hydroxylated substituents and the hydrophobic substituents described above. Such methods are well known in the art and are further illustrated in the examples. For example, the hydroxylated substituents and the hydrophobic substituents are introduced via their corresponding halogenated compounds by derivatizing the polyamine under alkaline conditions. Bromine is preferred as the halo atom in these compounds. In a preferred embodiment, this is achieved by the use of ap-bromohydroxyls and bromoalkanes or bromoaryls as the halo compounds. These two derivatizations may be done consecutively or in parallel using a mixture of the halohydroxyl compound and the halogenated hydrophobic compound. The mixing ratio of the halohydroxyl compound and the halogenated hydrophobic compound are suitably chosen for achieving the desired molar ratio of hydroxylated substituents and the hydrophobic substituents in the polyamine derivative to be prepared. In an approximation, the molar mixing ratio of the halohydroxyl compound and the halogenated hydrophobic compound in the parallel alkylation reaction corresponds to the molar ratio of hydroxylated substituents and the hydrophobic substituents in the modified polyamine, said molar ratio in the product obtained may be analysed e.g. by 1H-NMR. Deviations in the found molar ratio from the desired molar ratio may be used to adjust the mixing ratio of the halohydroxyl compound and the halogenated hydrophobic compound in order to obtain a modified polyamine having the desired molar ratio of hydroxylated substituents and hydrophobic moieties. It is clear to the skilled person that the desired degree of substitution (DOS) can be achieved and, if necessary, adjusted in a similar way by using suitable relative molar amounts of the halohydroxyl compound and the halogenated hydrophobic compound on the one hand to the amount of polyamine on the other hand. The reaction is generally carried out in an organic solvent, preferably a polar organic solvent such as alcohols.

In other embodiments the introduction of the hydroxylated substituents and hydrophobic substituents is achieved through acylation using the corresponding fatty acids and w-hydroxy acids or through Michael-addition using the respective unsaturated derivatives of the hydroxylated substituent and the hydrophobic compound.

Herein, structural formulae are given in the uncharged or non-ionised form. It is, however, clear to the skilled person that nitrogen atoms of these structures may be protonated, notably in aqueous solutions. Thus, compounds defined by way of any of these formulae also comprise the compounds or ions wherein any one of the nitrogen atoms is in a charged state.

The polyamine derivatives of the present invention are different from materials described in the state of the art. Wakefield et al. (2005) Bioconj Chem 16(5):1204-1208 report on copolymers from aminoethyl-vinylether and alkyl-vinylethers having alkyl groups with one to four carbon atoms. In contrast to the present invention, the polymers of Wakefield do not comprise hydroxyl moieties, they are thus missing an essential type of a functional group on the polymer. The polyamines of the present invention are also different from the modified polyethylenimines presented by van Vliet et al. (2008) in Chembiochem, 2008, 9, 1960-1967. There, polyethylenimines were systematically modified with dodecyl, benzyl and methyl moieties. Again, the essential hydroxyalkyl groups of the present invention are not used in van Vliet. In addition, extensive formation of quaternized amino groups occurs through the use of methyl iodide.

Use of Polyamine Derivatives as Transfectant

The modified polyamines such as the hydroxyalkyl-alkyl-polyamines of the invention are used for the transfection of polyanions into cells. Therefore, the polyamine derivatives are also referred to herein as transfectants of the invention. The polyanions can be selected from the group of peptides, proteins and nucleic acids. In certain embodiments the polyanions are proteins selected from antibodies. In specific embodiments the antibodies are of IgG type. In other embodiments antibody fragments are used, such as Fab, Fab', disulfide-linked F(ab')2 fragments or chemically linked F(ab')2 fragments or scFv fragments. In a preferred embodiment, the polyanions are nucleic acids.

Nucleic acids as used herein are polynucleotides or oligonucleotides, including, without limitation, DNA or RNA. Polynucleotide as used herein refers to any polyribonucleotide or polydeoxyribonucleotide, which may be of unmodified RNA or DNA or of modified RNA or DNA or of mixed DNA/RNA. Polynucleotides can be single or double stranded. A plasmid is an example for a double stranded polynucleotide, a mRNA is an example for a single stranded polynucleotide. Oligonucleotides as used herein are defined as molecules with two or more nucleotides, often more than three, and usually more than ten and less than a hundred which may be of unmodified RNA or DNA or of mixed DNA/RNA or of modified RNA or DNA, wherein the modifications include ring bridging such as found in LNA (locked nucleic acids), various modifications in the 2' position of the nucleoside such as 2'Me, 2'OMe, 2'MOE, 2'F and the like or wherein sugars other than ribose are used, such as arabinose in the 2'FANA nucleotides, glycerols in the unlocked nucleic acids or hexitol structures. The size of an oligonucleotide may depend on many factors, including the ultimate use of the oligonucleotide. Typical examples for oligonucleotides are siRNA, antisense inhibitors, miRNA, DNAzymes, aptamers and the like. Essentially, all nucleic acids carrying negative charges on their backbone are compatible for use with the transfectants of the invention, this includes various backbone-modified nucleic acids such those comprising phosphothioate linkages or phosphodithionate linkages. In contrast, uncharged nucleic acids such as those built from methylphosphonates or peptide-nucleic acids (PNA's) are less compatible with the transfectants of the invention.

Complex Formation Between Polyamine Derivatives and Polyanions

For transfecting a nucleic acid or other polyanion, a complex between the nucleic acid (or other polyanion) and the transfectant is generally made. The formation of complexes between transfection reagents and polyanions is known to the person skilled in the art. Generally, this may be achieved by combining a first solution comprising the transfectant and a second solution comprising the polyanion or nucleic acid. Typically, the number of cationic charges provided by the transfectant is higher than the number of negative charges on the polyanion. This ratio is known as an N/P ratio in the art, wherein N denotes the number of the formal nitrogen charges on the transfectant and P the number of phosphate groups on a nucleic acid. In some embodiments the N/P ratio for the use of hydroxyalkyl-alkyl-polyamines in combination with nucleic acids is between 2 and 20, in preferred embodiments such ratio is between 5 and 15 and in even more preferred embodiments the N/P ratio is about 10.

In other embodiments, the N/P ratio is between 2 and 6, more preferred around 4. Depending on the N/P ratio, the complexes between a nucleic acid and a polyamine derivative may have different charges and a different particles size. Complexes having a N/P value of about 10 or more have a neutral or slightly positive surface charge as determined by zeta potential measurements. The particle size of such complexes is between 200 and 1000 nm, in preferred embodiments between 250 and 500 nm as determined by dynamic light scattering.

Complexes having a N/P of about 6 or lower have a neutral to negative surface charge as determined by zeta potential measurements. The particle size of complexes having a N/P of about 6 or smaller is between 50 and 500 nm, in preferred embodiments between 100 and 200 nm as determined by dynamic light scattering.

It is well known to the person skilled in the art that the particle size and surface charge of a particle are determinants for the distribution of particles in the systemic circulation of a vertebrate animal, a mammal or in humans. Particles having a size of 150 nm or below are able to reach the liver parenchyma from the blood stream while large particles are excluded. In contrast, tumors, sites of inflammation or the stroma cells in the spleen can be reached by larger particles up to about 500 nm.

Complex formation between the transfectant of the invention and the polyanion to be transfected is generally carried out. Complex formation between the polyanions such as nucleic acid involves a charge interaction with the transfectant. Such interaction is achieved in aqueous solution in a pH range between 3 and 9 where both complex partners are ionized. In some embodiments the pH for complex formation is between 4 and 8 and in preferred embodiments said pH is between 5 and 7. The pH of the complex forming solution is adjusted by the use of one or more buffer substances. In principle, any buffer substance having a pK within the aforementioned range and being non-toxic to cells can be used. In preferred embodiments, buffers based on acetate, maleate, succinate, carbonates, phosphates, citrate, methylethylsulfonate (MES), Bis-Tris, Bis-Tris-propane, tris-(hydroxymethyl)aminomethan, tricine or buffers of the Good series such as HEPES, TES, MOPS, BES, MOPSO, ACES, PIPES, ADA, HEPPS are used. More preferred buffers are acetate, phosphates, citrate or HEPES.

The solution wherein the complex formation occurs may comprise other ingredients such as salts or sugars as long as these substances do not compete with the complex formation or are toxic to the cells. In preferred embodiments, the amount of salts is limited so that the total ionic strength of the solution is below 0.2 mol/L, in more preferred embodiments the ionic strength is below 0.1 mol/L. A salt well tolerated by cells is sodium chloride.

To avoid osmotic stress during the addition of the transfection complex to cells, sugars can be added to the complex forming solution to adjust the osmolarity. In some embodiments the addition of sugars is limited so that the total osmolarity of the solution added to the cells is between 150 and 500 mosm/L, in preferred embodiments the osmolarity is between 270 and 310 mosm/L. In preferred embodiments, glucose, sucrose or trehalose are used to adjust the osmolarity of the transfection mixture. It was surprisingly found that the transfection mixture can also be prepared using certain media with unknown composition. In many cases, the transfection mixture could be prepared with cell culture media, such as DMEM, Optimem (trademark of Life Technologies) and the like.

The transfectants of the present invention may have a limited solubility in water or buffered solutions. The solubility is a function of the pH and the accompanying ionization of the polyamine derivatives of this invention. As a general rule, these compounds have a better solubility in water upon acidification, e.g. in media having a pH of 7 or less. On the contrary, the polyamine derivatives are easily soluble in alcohols as for example ethanol, propanol, 1,2-dihydroxypropane or isopropanol (that are also referred to herein collectively as "short-chain alcohol") at pH of 9 or higher. Depending on the pH, it is also possible to employ mixtures of short-chain alcohols with water as a solvent, for example mixtures having between 33 and 100% of ethanol, propanol, 1,2-dihydroxypropane or isopropanol for less ionized forms of the transfectants or mixtures having between 0 and 66% of said alcohols for more ionized forms of the transfectants. In certain embodiments, the transfectants are stored as stock solutions containing between 20 and 200 mM (based nitrogen atoms in the transfectant) of the transfectant in lower alcohols. Working concentrations of about 0.1 mM to 5 mM of the transfectant may then be generated by dilution of the stock into an aqueous buffer solution. Typically, the shorter alcohols need not be removed from the transfection mixture and are tolerated by the cells.

In a specific embodiment, the transfectants are used under the following transfection protocol:
1) Polyamine derivatives are supplied as 50 mM solution (based on nitrogen content) in 96% ethanol
2) Transfection buffer comprising 10 mM sodium dihydrogenphosphate and 3 mM sodium hydroxide is prepared.
3) The modified polyamine is diluted in transfection buffer to a 1 mM solution.

4) siRNA is diluted in transfection buffer to 22 µM siRNA. Since the average number of phosphates on siRNA is about 45, the total concentration of phosphorus is about 1 mM
5) The working solutions of the polyamine and siRNA are combined in a 10+1 ratio which results in an N/P ratio of 10 and a concentration of the siRNA in the complexation mixture of 2 µM.
6) Up to 20 µl of the transfection mixture prepared in (5) is added per 100 µl of medium of cultivated cells.

In an alternative embodiment, the transfectants are used with the following general protocol:
1) Polyamine derivatives are supplied as 50 mM solution (based on monomer weight) in 96% ethanol.
2) Transfection buffer comprising 10 mM citric acid and 19 mM sodium hydroxide is prepared.
3) The modified polyamine is diluted in transfection buffer to a 1.8 mM solution.
4) siRNA is diluted in transfection buffer to 4 µM siRNA.
5) The working solutions of the polyamine and siRNA are combined in a 1+1 ratio which results in an N/P ratio of about 10 and a concentration of the siRNA during complexation of 2 µM.
6) Up to 20 µl of the transfection mixture prepared in (5) is added per 100 µl of medium of cultivated cells.

Transfectants having a small particle size can be prepared using the following general protocol 3:
1) Polyamine derivative is supplied as 56 mM solution (based on nitrogen content) in 33 to 100% ethanol, preferably 70% ethanol.
2) Transfection buffer comprising 10 mM sodium dihydrogenphosphate and 3 mM sodium hydroxide is prepared.
3) siRNA is diluted in transfection buffer to 18 µM siRNA. Since the average number of phosphates on siRNA is about 45, the total concentration of phosphorus is about 0.75 mM
4) The siRNA solution is added directly to the modified polyamine in a 20+1 ratio which results in an N/P ratio of 4 and a concentration of the siRNA in the complexation mixture of 17 µM.
5) Up to 10 µl of the transfection mixture is added per 100 µl of medium of cultivated cells or administered to animals.

While the preparation of transfection complexes from two solutions is often performed, it requires the separate preparation of the solutions containing transfectant and nucleic acid. The solutions need to be clean or sterile for their work in cell culture; they may also have a limited shelf life. A further improvement is the use of a dry transfectant that is reconstituted with transfection buffer before use. For this purpose, the transfectant can be dried down from its solution in short-chain alcohols. A particular benefit of such method is the provision of small and defined aliquots of transfectant having a very long shelf life. The dry transfectant can be rehydrated with transfection buffer. In some embodiments, the dry transfectant may also be rehydrated with a solution already containing the nucleic acid.

In other embodiments, the transfectant is provided in a lyophilized form. In a preferred aspect of such embodiment the transfectant is lyophilized from a solution comprising a buffer system adjusted to yield a pH between 5 and 7 and further comprising a sugar in an amount to yield a total osmolarity of between 100 and 500 mosm/L upon reconstitution, e.g. 270 mM sucrose or trehalose or glucose. In this embodiment, the nucleic acid is provided as a dilute aqueous solution and used directly for the reconstitution of the lyophilized transfectant, so that hydration and complex formation occur in a single step. The resultant transfection mixture can then directly be added to the cells to be transfected. In another embodiment, the transfectant is lyophilized from a solution further comprising a sugar in an amount to yield an osmolarity of between 100 and 500 mosm/L upon reconstitution, e.g. 270 mM sucrose or trehalose or glucose and the nucleic acid is provided in a transfection buffer lacking the sugar. The lyophilized transfectant is then rehydrated with the nucleic acid solution containing the buffer components, so that rehydration and complex formation occur simultaneously and the number of pipetting steps is reduced.

Kits Comprising Transfectants

The transfectants of this invention can be marketed in the form of a kit, optionally further comprising a siRNA for control reactions.

In a first embodiment, the kit contains the following:
A) A solution of transfectant in a short-chain alcohol, wherein the alcohol may be 96% ethanol and the transfectant may have a concentration of about 50 mM (based on nitrogen atoms in the transfectant),
B) A buffer solution having a pH between 4 and 8 and an ionic strength below 0.2, preferably below 0.1,
C) A manual with complete instructions, optionally also a short manual with condensed instructions In a second embodiment, such a kit comprises the following:
A) A solution of the transfectant as described in the first embodiment, wherein the solution is divided into aliquots. Preferentially, the number of aliquots is between 5 and 100, more preferred the number of aliquots is between 6 and 20. It is further preferred that each aliquot contains between 10 and 1000 nmol transfectant (based on monomer),
B) A buffer solution having a pH between 4 and 8 and an ionic strength below 0.2, preferably below 0.1,
C) A manual with complete instructions, optionally also a short manual with condensed instructions In a third embodiment, such kit comprises the following:
A) A solution of the transfectant as described in the first embodiment, wherein the solution is divided into aliquots and wherein such aliquots are arrayed in a microplate having between 6 and 1576 wells, preferably 24, 96 or 384 wells, and wherein each aliquot contains between 10 and 1000 nmol transfectant,
B) A buffer solution having a pH between 4 and 8 and an ionic strength below 0.2, preferably below 0.1,
C) A manual with complete instructions, optionally also a short manual with condensed instructions In a fourth embodiment, such a kit comprises the following:
A) A dry transfectant divided into aliquots. Preferentially, the number of aliquots is between 5 and 100, more preferred the number of aliquots is between 6 and 20. It is further preferred that each aliquot contains between 10 and 1000 nmol transfectant (based on monomer),
B) A buffer solution having a pH between 4 and 8 and an ionic strength below 0.2, preferably below 0.1,
C) A manual with complete instructions, optionally also a short manual with condensed instructions In a fifth embodiment, such a kit comprises the following:
A) A dry transfectant divided into aliquots, wherein such aliquots are arrayed in a microplate having between 6 and 1576 wells, preferably the microplate has 24, 96 or 384 wells, and wherein each aliquot contains between 10 and 1000 nmol transfectant, B) A buffer solution having a pH between 4 and 8 and an ionic strength below 0.2, preferably below 0.1,
C) A manual with complete instructions, optionally also a short manual with condensed instructions In a sixth embodiment, such a kit comprises the following:
A) A lyophilized transfectant divided into aliquots. Preferentially, the number of aliquots is between 5 and 100, more preferred the number of aliquots is between 6 and 20. It is further preferred that each aliquot contains between 10 and 1000 nmol transfectant (based on monomer),
B) A buffer solution having a pH between 4 and 8 and an ionic strength below 0.2, preferably below 0.1,
C) A manual with complete instructions, optionally also a short manual with condensed instructions In a seventh embodiment, such kit comprises the following:
A) A lyophilized transfectant divided into aliquots, wherein such aliquots are arrayed in a microplate having between 6 and 1576 wells, preferably 24, 96 or 384 wells, and wherein each aliquot contains between 10 and 1000 nmol transfectant,
B) A buffer solution having a pH between 4 and 8 and an ionic strength below 0.2, preferably below 0.1,
C) a manual with complete instructions, optionally also a short manual ith condensed instructions In certain aspects of the third, fifth and seventh embodiment, all wells of such microplate contain the same amount of transfectant. In other aspects, the wells contain different amounts of transfectant. Such designs may involve gradients of the transfectants in neighboring wells which is useful during the optimization of N/P ratios with the nucleic acids. In yet other aspects, certain wells may be empty, e.g. for the generation of serial dilutions from a complexation mixture. FIGS. 1 to 4 further illustrate such designs of arrayed amounts of transfectants on the example of a 96 well plate.

Lyophilized Complexes of Transfectant and Nucleic Acid

In yet other embodiments the complexes of the polyamine derivative of this invention with one or more nucleic acids are formed and lyophilized and marketed as a complete product. This solution offers an even higher degree of integration compared to currently commercialized products. It also provides an opportunity to centralize the quality control of the product including its particle formation at the site of the manufacturer. Other advantages of the lyophilized complexes are their long storage stability and the absence of the short-chain alcohols used as solvent for the modified polyamines.

The lyophilized complexes between a polyamine derivative and one or more nucleic acids are of particular advantage for in vivo applications including animal research or for therapeutic use.

Lyophilized complexes can be manufactured with any of the general methods 1 to 3 described above with the inclusion of an lyophilization and rehydration step after the complexation.

In a specific embodiment, the complexes between the modified polyamines of the invention and one or more nucleic acids are prepared under the following protocol 4:
1) Modified polyamine is supplied as 50 mM solution (based on nitrogen content) in 33 to 100% ethanol
2) Transfection buffer comprising 10 mM sodium dihydrogenphosphate and 3 mM sodium hydroxide is prepared.
3) The modified polyamine is diluted in transfection buffer to a 1 mM solution.
4) siRNA is diluted in transfection buffer to 22 µM siRNA. Since the average number of phosphates on siRNA is about 45, the total concentration of phosphorus is about 1 mM
5) The working solutions of the polyamine and siRNA are combined in a 10+1 ratio which results in an N/P ratio of 10 and a concentration of the siRNA in the complexation mixture of 2 µM.
6) The complexes are optionally divided into aliquots, lyophilized, sealed with an air-tight seal and stored.
7) The lyophilized complexes are rehydrated with water.
8) Up to 20 µl of the rehydrated complex is added per 100 µl of medium of cultivated cells or the rehydrated complexes are administered to an animal or human being.

In a specific embodiment, the complexes between the modified polyamines of the invention and one or more nucleic acids are prepared under the following protocol 5:
1) Modified polyamine is supplied as 56 mM solution (based on nitrogen content) in 33 to 100% ethanol
2) Transfection buffer comprising 10 mM sodium dihydrogenphosphate and 3 mM sodium hydroxide is prepared.
3) siRNA is diluted in transfection buffer to 18 µM siRNA. Since the average number of phosphates on siRNA is about 45, the total concentration of phosphorus is about 0.75 mM
4) The siRNA solution is added directly to the modified polyamine in a 20+1 ratio which results in an N/P ratio of 4 and a concentration of the siRNA in the complexation mixture of 17 µM.
5) The complexes are optionally divided into aliquots, lyophilized, sealed with an air-tight seal and stored.
6) The lyophilized complexes are rehydrated with water
7) Up to 10 µl of the rehydrated complex is added per 100 µl of medium of cultivated cells or the rehydrated complexes are administered to an animal or a human being.

The administration of complexed nucleic acids to animals or human beings is known to persons skilled in the art and the complexed nucleic acids may be administered systemically or topically in doses required for the specific indication. The amounts of nucleic acid administered may vary between 0.1 µg and 100 mg per kg of body weight and can be administered once or multiple times or in complex or intermittent dosing regimens such a daily dosing, a dosing every other day or 3 times a week, once a week or once a month or a combination of such regimens.

DESCRIPTION OF THE FIGURES

FIGS. 1-4 show various designs for transfectants arrayed in microplates. The numbers in the schematic microplates denote an amount of transfectant in nmol (based on nitrogens) deposited in each well. The figures take 96 well plates as an example and place the transfectants in certain vertical rows. It is understood that similar designs can easily be derived from this general structure, e.g. where the patterns are organized horizontally, with more or less empty wells, with partial use of the plate and the like.

FIG. 1 Amount of transfectant in nmol placed into certain wells of a 96 well plate, even distribution.

FIG. 2 Amount of transfectant in nmol placed into certain wells of a 96 well plate, to simplify optimization of the N/P ratio.

FIG. 3 Amount of transfectant in nmol placed into certain wells of a microplate, including empty wells for serial dilutions of the transfection complexes.

FIG. 4 Amount of transfectant in nmol placed into certain wells of a microplate, facilitating a simple optimization of the N/P ratio and serial dilution of the transfection complexes.

EXAMPLES

The invention is now further illustrated with the following examples without being limited to these.

Example 1

Modification of Polyamines

Linear PEI (free base) having an average molecular mass of 2 kDa or 25 kDa was from Polysciences. Branched PEI (free base) of 10 kDa size was from Aldrich. The polymers were dissolved in absolute ethanol at a concentration of 250 mono-mM; that is the concentration of nitrogens was 250 mM. Propylbromide, hexylbromide, nonylbromide and dodecylbromide (all from SIGMA) were dissolved in absolute ethanol at 250 mM and 3-bromopropanol, 4-bromobutanol, 5-bromopentanol, 6-bromohexanol, 9-bromononaol and 12-bromododecanol were dissolved in absolute ethanol at 500 mM. $K_2CO_3$ was used as a 6 M solution in water.

For the modification of 100 μmol polyamine (based on nitrogen atoms in the transfectant), the following solutions were pipetted per reaction:
400 μl polyamine solution
X μl of the ω-bromoalcohol
Y μl of the 1-bromoalkane
ethanol up to 650 μl
33 μl $K_2CO_3$ All mixtures were sealed and incubated for 7 days at 60° C. in an oven. For initial tests, small aliquots of the reaction mixture were taken and diluted 1:100 in 75% ethanol/water. 42 μl of each diluted sample were transferred into a 96 well plate and dried.

Example 2

Complexation with siRNA

Modified polyamines were hydrated for 20 min in 50 μl of buffer pH4 (10 mM HAc, 10 mM NaH2PO4, pH4 with NaOH). 50 μl of a siRNA (2 μM in buffer pH4) were added and after 2-3 min the polymer-siRNA solution was brought to pH7 using 10 μl of 160 mM NaOH.

Example 3

Cultivation of Cells

HeLa cells were cultivated in 100 μl of RPMI1640 medium (PAA Lab GmbH) supplemented with 10% FCS (Sigma-Aldrich), 1×Pen/Strep (PAA lab GmbH) solution (according to the instructions of the manufacturer) and seeded at a density of 4000 cells/well in a 96 well-plate. The density of live cells was measured using the Countess Cell counter (Invitrogen). Cells were cultivated in a humidified incubator at 37° C. and 5% $CO_2$. 24 h after plating cells were supplied with fresh complete medium and transfected the same day.

Example 4

Transfection of Cells

HeLa cells were transfected with the polyamine-siRNA-complexes by transferring 10 μl material as obtained under example 2 per well. This addition results in a concentration of 100 nM PLK-1 siRNA in the cell culture medium. Cells were cultivated for three days at 37° C. and 5% $CO_2$ in a humidified incubator without a change of the cultivation medium.

Example 5

Type of siRNA

The siRNA used here is targeting the PLK-1 gene, the product of which is an essential component in the cell cycle. Downregulation of the target protein results in mitotic arrest and apoptosis. The transfection of cells is therefore monitored using a cell viability assay. The siRNA targeting PLK-1 and an unrelated control siRNA used herein were published by Haupenthal et al. (2007) Int J Cancer, 121, 206-210.

Example 6

Viability Assay

Cells were tested for viability after three days by using the Cell Titer Blue assay (CTB, Promega). The medium was discarded and cells were supplied with fresh complete medium supplemented with the CTB reagent (5:1, vol/vol). 90-100 min after incubation at 37° C. and 5% $CO_2$ in a humidified incubator the samples were transferred to a black fluorescence plate and color change of the samples was measured by a fluorescence reader at Ex560 nm/Em590 nm. The signal was normalized to 100% using untreated cells grown on the same culture plate and 0% with wells in which no cells were seeded.

Example 7

Transfection with Modified Polyamines

The following tables show the % of live cells relative to an untreated culture as a metric for the PLK-1 downregulation following cell transfection. Measurements using the unrelated, non-targeting siRNA were performed in parallel and the ratio of both values (PLK-1/control) is shown here as the S/N ratio. Unspecific reactions of the transfection complexes is characterized by S/N ratios around 1, specific reactions have S/N ratios substantially below 1. For better readability, S/N values below 0.7 were highlighted. DOS values are calculated from the molar ratios of ω-bromoalcohol and 1-bromoalkane used to polyamine according to Example 1.

TABLE 4

Transfection using modified linear polyethylenimine, 2 kDa

| PEI 2k, only hydroxyalkylation | | | | | | | |
|---|---|---|---|---|---|---|---|
| PLK-1 | | | | S/N | | | |
| Hydroxy-alkyl type | DOS | | | Hydroxy-alkyl type | DOS | | |
| | 30% | 60% | 100% | | 30% | 60% | 100% |
| C2 | 84 | 83 | 73 | C2 | 1.0 | 1.0 | 1.0 |
| C3 | 89 | 89 | 79 | C3 | 1.0 | 1.0 | 1.0 |
| C4 | 95 | 93 | 91 | C4 | 1.1 | 1.1 | 1.0 |
| C5 | 96 | 93 | 89 | C5 | 1.0 | 1.0 | 1.0 |
| C6 | 97 | 99 | 104 | C6 | 1.0 | 1.0 | 1.0 |
| C9 | 28 | 80 | 95 | C9 | 1.0 | 0.9 | 1.0 |

TABLE 4-continued

Transfection using modified linear polyethylenimine, 2 kDa

PEI 2k, only alkylation

| Alkyl type | PLK-1 DOS 15% | 30% | 50% | Alkyl type | S/N DOS 15% | 30% | 50% |
|---|---|---|---|---|---|---|---|
| C3 | 101 | 105 | 106 | C3 | 1.0 | 1.0 | 1.0 |
| C6 | 91 | 61 | 64 | C6 | 1.0 | 0.9 | 0.9 |
| C9 | 94 | 37 | 107 | C9 | 1.0 | 0.8 | 1.0 |
| C12 | 53 | 92 | 112 | C12 | 1.0 | 0.9 | 1.0 |

PEI2k, combined hydroxyalkylation and alkylation

| Hydroxyalkyl | C9 |
|---|---|
| Alkyl | C3-C12 |
| O/A | 2.7 |

| Alkyl type | PLK-1 DOS 23% | 47% | 78% | Alkyl type | S/N DOS 23% | 47% | 78% |
|---|---|---|---|---|---|---|---|
| C3 | 25 | 24 | 21 | C3 | 1.1 | 0.8 | 0.9 |
| C6 | 24 | 20 | 44 | C6 | 0.8 | 1.0 | 1.0 |
| C9 | 25 | 20 | 83 | C9 | 1.1 | 0.4 | 0.9 |
| C12 | 38 | 58 | 78 | C12 | 1.8 | 1.1 | 0.8 |

TABLE 5

Transfection using modified linear polyethylenimine, 25 kDa

PEI 25k, only hydroxyalkylation

| Hydroxyalkyl | PLK-1 DOS 30% | 60% | 100% | Hydroxyalkyl | S/N DOS 30% | 60% | 100% |
|---|---|---|---|---|---|---|---|
| C2 | 91 | 92 | 84 | C2 | 1.0 | 1.0 | 1.0 |
| C3 | 98 | 94 | 89 | C3 | 1.1 | 1.2 | 1.0 |
| C4 | 94 | 93 | 93 | C4 | 1.0 | 1.0 | 1.0 |
| C5 | 88 | 87 | 83 | C5 | 1.0 | 1.1 | 1.0 |
| C6 | 100 | 91 | 92 | C6 | 1.1 | 1.0 | 1.0 |
| C9 | 27 | 86 | 90 | C9 | 1.0 | 1.1 | 1.0 |

PEI 25k, only alkylation

| Alkyl | PLK-1 DOS 15% | 30% | 50% | Alkyl | S/N DOS 15% | 30% | 50% |
|---|---|---|---|---|---|---|---|
| C3 | 107 | 101 | 100 | C3 | 1.1 | 1.0 | 1.0 |
| C6 | 42 | 43 | 42 | C6 | 1.0 | 1.1 | 1.1 |
| C9 | 67 | 55 | 101 | C9 | 1.0 | 1.0 | 1.0 |
| C12 | 56 | 93 | 109 | C12 | 0.9 | 1.0 | 1.0 |

PEI25k, combined hydroxyalkylation and alkylation

| Hydroxyalkyl | C5 |
|---|---|
| Alkyl | C3-C12 |
| O/A | 0.8 |

| Alkyl | PLK-1 DOS 19% | 38% | 64% | Alkyl | S/N DOS 19% | 38% | 64% |
|---|---|---|---|---|---|---|---|
| C3 | 96 | 96 | 97 | C3 | 1.1 | 1.1 | 1.1 |
| C6 | 76 | 40 | 31 | C6 | 1.2 | 1.4 | 0.4 |
| C9 | 87 | 82 | 39 | C9 | 1.0 | 0.8 | 0.5 |
| C12 | 91 | 38 | 33 | C12 | 1.0 | 0.5 | 0.7 |

TABLE 6

Transfection using modified branched polyethylenimine, 10 kDa branched PEI 10k, only hydroxyalkylation

| Hydroxyalkyl | PLK-1 DOS 30% | 60% | 100% | Hydroxyalkyl | S/N DOS 30% | 60% | 100% |
|---|---|---|---|---|---|---|---|
| C2 | 81 | 83 | 85 | C2 | 1.0 | 1.0 | 1.1 |
| C3 | 81 | 83 | 84 | C3 | 1.0 | 1.0 | 1.1 |
| C4 | 82 | 82 | 85 | C4 | 1.0 | 0.9 | 1.0 |
| C5 | 88 | 89 | 88 | C5 | 1.0 | 1.0 | 1.0 |
| C6 | 77 | 75 | 84 | C6 | 0.9 | 0.9 | 0.9 |
| C9 | 27 | 46 | 57 | C9 | 1.0 | 1.1 | 0.9 | branched PEI 10k, only alkylation

| Alkyl | PLK-1 DOS 15% | 30% | 50% | Alkyl | S/N DOS 15% | 30% | 50% |
|---|---|---|---|---|---|---|---|
| C3 | 88 | 88 | 90 | C3 | 0.9 | 0.9 | 1.0 |
| C6 | 42 | 32 | 29 | C6 | 0.6 | 0.6 | 0.5 |
| C9 | 38 | 37 | 102 | C9 | 0.6 | 0.7 | 1.0 |
| C12 | 57 | 103 | 103 | C12 | 0.8 | 1.0 | 1.0 | branched PEI 10k, combined hydroxyalkylation and alkylation

| Hydroxyalkyl | C9 |
|---|---|
| Alkyl | C3-C12 |
| O/A | 1.5 |

| Alkyl | PLK-1 DOS 21% | 42% | 71% | Alkyl | S/N DOS 21% | 42% | 71% |
|---|---|---|---|---|---|---|---|
| C3 | 36 | 26 | 32 | C3 | 0.9 | 1.0 | 1.1 |
| C6 | 29 | 31 | 83 | C6 | 1.1 | 0.6 | 1.1 |
| C9 | 31 | 34 | 66 | C9 | 0.7 | 0.6 | 0.8 |
| C12 | 29 | 15 | 74 | C12 | 0.9 | 0.4 | 0.8 |

The polyethylenimines used here are inactive transfectants under the assay conditions. A single modification with either alkyl or hydroxyalkyl moieties may reduce the cell viability; this is typically the case for the long-chain alkyl or hydroxyalkyl moieties. However, these effects are unspecific throughout the test panel as demonstrated by the S/N values which are around 1 in all these cases.

The combined modification with both hydroxyalkyl and alkyl moieties displays greater activity on cells, it reduces the cell viability to a greater extent. Most importantly, the co-modified polymers now mediate a specific effect of the coding siRNA against PLK-1 with S/N ratios that are frequently well below 1.

Example 8

Transfection Efficiency on Different Cell Types

Transfectant: branched PEI was modified with 9-bromononanol and dodecylbromid as described in example 1.

The reaction was fed to achieve a degree of substitution about 45%, the ratio between the modifiers was about 3. Modified PEI was purified from the reaction mixture using size exclusion chromatography.

Complexation: Purified transfectant was provided in a solution containing 30% ethanol and 10 mM NaOH. Polymers were diluted in buffer D (10 mM citrate, adjusted to pH5.0 with NaOH) or buffer F (10 mM phosphate, adjusted to pH6.5 with NaOH) to a concentration of 4 mM. To obtain a NP-ratio of 10, 150 µl of the diluted polymers were complexed with 150 µl of 10 µM siRNA solution (Plk1 or scrambled control) in buffer D or F. Serial dilutions of these complexes were made in the respective buffers in a 96 well-plate to obtain concentrations from 500 nM to 2 nM on cells.

Transfection: Cells were transfected with the polymer-siRNA-complexes by transferring a volume of 10 µl/well from the "complexation plate" to the cell plate (column 1-10). Cells were cultivated for three days at 37° C. and 5% CO2 in a humidified incubator without a change of the cultivation medium.

Viability assay: Cells were tested for viability after three days by using the Cell Titer Blue assay (CTB, Promega). The medium was discarded and cells were supplied with fresh complete medium supplemented with the CTB reagent (120 µl, 5:1, vol/vol). For NIH3T3, Jurkat and THP-1 cells the CTB-medium reagent was added directly to the cell medium, without discarding. 90-100 min (240 min for NIH3T3, Jurkat and THP-1 cells) after incubation at 37° C. and 5% CO2 in a humidified incubator the samples were transferred to a black fluorescence plate and color change of the samples was measured by a fluorescence reader at Ex560 nm/Em590 nm.

TABLE 7

List of cell types

| Name | Type | Species | Growth | Source |
|---|---|---|---|---|
| HeLa | Cervix-Carcinom | Human | adherent | DSMZ |
| HepG2 | Hepato-Carcinom | Human | adherent | CLS |
| HEK-293 | Embryonic kidney | Human | adherent | CLS |
| Neuro 2a | Neuroblastom | Mouse | adherent | CLS |
| A549 | Lung adenocarcinom | Human | adherent | BSH |
| NIH3T3 | Embryonic fibroblast | Mouse | adherent | BSH |
| THP-1 | Monozytic leukaemia | Human | Suspension | CLS |

The performance of the modified polyamine was measured as EC50, the concentration of siRNA needed for an inhibition of cell growth of 50%. In parallel, the same test was carried out using an unrelated siRNA and the EC50 value was also calculated. The signal-to-noise ratio is then defined as the ratio between the EC50 (control) and EC50 (PLK-1).

TABLE 8

Transfection and signal-to-noise ratio for a modified polyamine

| Cell type | EC50 (PLK-1, nM) | EC50 (CTR, nM) | Signal/Noise |
|---|---|---|---|
| HeLa | 14 | 88 | 6 |
| HepG2 | 126 | 862 | 7 |
| Neuro2A | 23 | 110 | 5 |
| CHO | 67 | 449 | 7 |
| HEK293 | 104 | >1300 | >13 |
| A549 | 80 | 690 | 9 |
| THP-1 | 59 | 217 | 4 |

The data demonstrate a very efficient transfection of the siRNA into different cell types, including cell growing in suspension. The transfection reaction is very well tolerated by the cells with little or almost no signs of toxicity, indicated by signal-to-noise ratios of 4 or higher.

Example 9

Transfection Efficiency and Signal-to-noise Ratio of Commercial Reagents

In the same experiment as described in example 8, several commercial transfectants were tested in parallel, the results of such test are listed in table 9.

Commercial Transfectants: Interferin (Polyplus, France), Ribocellin (BioCellChallenge, Germany), TransIT-TKO (Mirus, US), siPort NeoFX (Ambion/Life technologies Corp.), Dharmafect (Dharmacon/Thermo Fisher) and Lipofectamine RNAiMAX (Invitrogen/Life Technologies Corp.) were handled and complexed to Plk1 and scr siRNA according to the manufacturer's instructions. Serial dilutions were made in Optimem I (Gibco/Life Technologies) to obtain siRNA concentrations from 100 nM to 2 nM on cells.

TABLE 9

Transfection and signal-to-noise ratio for commercial reagents

| | Reagent | | | | | | | | |
|---|---|---|---|---|---|---|---|---|---|
| | siPort NeoFX | | | Dharmafect | | | RNAiMAX | | |
| Cell | EC50 (nM) | | | EC50 (nM) | | | EC50 (nM) | | |
| type | PLK | SCR | S/N | PLK | SCR | S/N | PLK | SCR | S/N |
| HeLa | 42 | >100 | 3 | 13 | 24 | 2 | 57 | 300 | 5 |
| HepG2 | 500 | 211 | 0 | 94 | 95 | 1 | 153 | 326 | 2 |
| Neuro | 500 | >500 | n.a. | 159 | 144 | 1 | 360 | 0 | 0 |
| CHO | >500 | >500 | n.a. | 13 | 27 | 2 | 43 | 204 | 5 |
| HEK | >500 | >500 | n.a. | 112 | 260 | 2 | 164 | >500 | n.a. |
| A549 | 500 | >500 | n.a. | 21 | 42 | 2 | 88 | 137 | 2 |
| THP1 | 500 | >500 | n.a. | 21 | 35 | 2 | >500 | >500 | n.a. |

Although transfection could be achieved in many cases in particular with the reagents Dharmafect and RNAiMAX, the signal-to-noise ratios are much lower throughout the test.

Example 10

Analytical Characterization

Transfectant: 5 mmol of branched PEI was modified with 9-bromononanol and dodecylbromid as described in example 1, all other reagents were brought to scale. The targeted degree of substitution was about 45%, the ratio between the modifiers about 1.5. Modified PEI was purified from the reaction mixture using size exclusion chromatography in 10 mM NaOH, 96% ethanol.

Analysis: 1 mL of the solution containing the analyte was mixed with 0.5 mL of 100 mM methoxyacetic acid and 25 µl of 2N NaOH. The mixture was dried under vacuum, dissolved in 700 µl CD3OD and analyzed by 1H NMR. Signals: methoxyacetic acid 4.0 ppm; bPEI backbone 2.5-2.8 ppm, terminal CH3 of the alkyl moiety 0.8 ppm and terminal CH2-OH of the hydroxyalkyl 3.2 ppm.

TABLE 10

Analysis of the 1H-NMR spectrum

| Signal | | example 10 | methoxy-acetic acid |
|---|---|---|---|
| Methoxyacetic acid | integral | | 200 |
| | μmol | | 50 |
| PEI backbone | integral | 656.1 | |
| | μmol | 82 | |
| —CH3 | integral | 68.7 | |
| | μmol | 11.45 | |
| —CH2—OH | integral | 73.9 | |
| | μmol | 18.48 | |
| O/A | | 1.61 | |
| Total DOS | | 36.5% | |

Example 11

More Polyamine Derivatives

The following polyamines were subjected to the modification reaction outlined in example 1:

TABLE 11

Polyamines

| Polymer | Architecture | Molecular weight | Source |
|---|---|---|---|
| PEI (free base) | Linear | 250 kDa | Polysciences, Cat 24314 |
| Polyethylenimine (free base) | Branched | 1.2 kDa | Polysciences, Cat 06088 |
| PEI (30% solution in water) | Branched | 70 kDa | Polysciences, Cat 06090 |

The polymers were dissolved in absolute ethanol at a concentration of 250 mono-mM; that is the concentration of nitrogen was 250 mM.

The hydroxyl compounds for the modification of polyamines were chosen from the following table 12 and were dissolved in absolute ethanol at a concentration of 250 mM:

TABLE 12

Hydroxyl compounds for the modification of polyamines.

| Hydroxyl Compound | Symbol | Type | Source |
|---|---|---|---|
| 2-bromoethanol | O2 | n-alkyl | Sigma B65586 |
| 4-bromobutanol | O4 | n-alkyl | Aldrich 95517 |
| 6-bromohexanol | O6 | n-alkyl | Aldrich 186481 |
| 9-bromononanol | O9 | n-alkyl | Aldrich 448729 |
| 12-bromododecanol | O12 | n-alkyl | Aldrich 224677 |

The hydrophobic compounds for the modification of the polyamines were chosen from the following table 13 and were also dissolved in absolute ethanol at a concentration of 250 mM:

TABLE 13

Hydrophobic compounds for the modification of polyamines.

| Hydrophobic Compound | Symbol | Type | Source |
|---|---|---|---|
| Propylbromide | A3 | n-alkyl | SIGMA B78106 |
| Hexylbromide | A6 | n-alkyl | Aldrich B68240 |
| Nonylbromide | A9 | n-alkyl | Aldrich B74607 |
| Dodecylbromide | A12 | n-alkyl | Aldrich B65551 |
| Benzylbromide | BB | Aryl | SIGMA B17905 |
| 2-bromoethylbenzene | 2-BEB | Alkylaryl | SIGMA B65780 |
| 4-isopropylbenzylbromide | 4-IPBB | Alkylaryl | Aldrich 563285 |
| 1-bromo-2-cyclohexylethane | B2CHE | Cyclic Alkyl | Aldrich 467952 |

$K_2CO_3$ was used as a 6 M solution in water.

For the modification of 100 μmol polyamine (based on monomer), the following solutions were pipetted per reaction:

400 μl polyamine solution
X μl of the brominated hydroxyl compound
Y μl of the brominated hydrocarbon compound
Absolute ethanol up to 650 μl
33 μl $K_2CO_3$ The combined amounts of X+Y were chosen for a degree of substitution of the amino groups of the polyamine between 0 and 100% and X and Y were further selected to complement each other and give various O/A ratios between 0 (only hydrophobic substituents) and the exclusive use of the hydroxylated substituent, denoted as O/A=99 in the tables below.

All mixtures were sealed and incubated for 7 days at 60° C. in an oven. Then, 250 μl of 2N NaOH were added, the mixtures were sealed again and incubated for another 2 days at 60° C. For intial tests, small aliquots of the reaction mixture were taken and diluted 1:100 in 75% ethanol/water. 42 μl of each diluted sample were transferred into a 96 well plate and dried.

Example 12

Transfection of siRNA Using Modified Polyamines

The modified polyamines from example 11 were complexed with siRNA targeting PLK-1 and tested for their transfection properties as described in the examples 2 to 6 with the exception of using Buffer F (10 mM NaH2PO4, 225 mM sucrose, pH7.2 (adjusted with NaOH)) for siRNA complexation and transfection. The results of the transfection reactions are described in the table 14.

TABLE 14 transfection of siRNA using certain polyamines wherein the hydrophobic group is an alkyl or aryl. Lower numbers indicate successful transfection of the cells and are highlighted for values <=50.

| Polymer | Mol weight in kDa | Hydroxy moiety | Hydrophobic moiety | DOS | % cell viability at certain O/A ratios | | | | | | |
|---|---|---|---|---|---|---|---|---|---|---|---|
| | | | | | 99 | 6 | 2.5 | 1.3 | 0.75 | 0.4 | 0.16 | 0 |
| bPEI | 1.2 | O9 | A3 | 0.5 | 5 | 13 | 46 | 79 | 72 | 72 | 74 | 79 |
| | | O6 | BB | 0.5 | 92 | 73 | 96 | 12 | 13 | 86 | 79 | 89 |
| | | O6 | 2-BEB | 0.5 | 98 | 90 | 104 | 85 | 16 | 101 | 84 | 66 |

TABLE 14-continued transfection of siRNA using certain polyamines wherein the hydrophobic group is an alkyl or aryl.
Lower numbers indicate successful transfection of the cells and are highlighted for values <=50.

| Polymer | Mol weight in kDa | Hydroxy moiety | Hydrophobic moiety | DOS | % cell viability at certain O/A ratios | | | | | | | |
|---|---|---|---|---|---|---|---|---|---|---|---|---|
| | | | | | 99 | 6 | 2.5 | 1.3 | 0.75 | 0.4 | 0.16 | 0 |
| bPEI | 70 | O6 | A6 | 0.5 | 68 | 26 | 3 | 3 | 18 | 94 | 23 | 70 |
| | | O6 | A9 | 0.5 | 63 | 4 | 48 | 79 | 69 | 63 | 63 | 56 |
| | | O9 | A3 | 0.5 | 8 | 1 | 1 | −1 | 1 | 61 | 48 | 77 |
| | | O9 | A9 | 0.25 | 27 | 5 | 9 | 53 | 64 | 68 | 68 | 80 |
| | | O2 | BB | 0.5 | 96 | 98 | 91 | 68 | 21 | 79 | 77 | 80 |
| | | O2 | 4-IPBB | 0.5 | 95 | 94 | 83 | 48 | 66 | 59 | 58 | 62 |
| | | O4 | BB | 0.5 | 92 | 73 | 96 | 12 | 13 | 86 | 79 | 89 |
| | | O4 | 4-IPBB | 0.5 | 100 | 100 | 31 | 32 | 44 | 46 | 61 | 75 |
| lin PEI | 250 | O6 | A6 | 0.5 | 84 | 79 | 51 | 48 | 62 | 67 | 68 | 87 |
| | | O9 | A3 | 0.35 | 10 | 0 | 19 | 40 | 40 | 100 | 78 | 86 |
| | | O9 | A6 | 0.25 | 45 | 9 | 57 | 69 | 57 | 88 | 66 | 74 |
| | | O9 | A9 | 0.25 | 66 | 25 | 45 | 81 | 75 | 80 | 65 | 84 |
| | | O2 | BB | 0.5 | 87 | 100 | 63 | 79 | 67 | 74 | 13 | 29 |
| | | O9 | BB | 0.5 | 112 | 23 | 3 | 3 | 3 | 118 | 100 | 123 |
| | | O9 | 2-BEB | 0.5 | 110 | 36 | 3 | 10 | 2 | 19 | 20 | 103 |
| | | O9 | 4-IPBB | 0.5 | 119 | 4 | 1 | 16 | 23 | 61 | 95 | 62 |
| | | O9 | B2CHE | 0.5 | 106 | 11 | 11 | 3 | 1 | 16 | 24 | 103 |

The data of this table 14 demonstrate that many of the modified polyamines are capable of transfecting cells with siRNA. The hydrophobic group was selected from aliphatic or cyclic alkyl moieties or from various aryl components and all resulted in the formation of active carriers regardless of their structural differences.

The active carriers were formed from polyamines having widely different molecular weights, and different architecture (linear or branched). It is also apparent from the data that the hydroxyl and hydrophobic components act synergistically, while single modifications contribute little, if any, to the carrier properties.

Example 13

Transfection of Plasmids

Cell culture: HeLa cells were cultivated in 100 µl of RPMI1640 medium (PAA Lab GmbH) supplemented with 10% FCS (Sigma-Aldrich), 1×Pen/Strep (PAA lab GmbH) solution (according to the manufacturer instructions) and seeded at 8000 cells/well of a 96well-plate. Cells were cultivated in a humidified incubator at 37° C. and 5% CO2. 24 h after plating cells were supplied with fresh complete medium and transfected the same day.

Complexation: Polyamines were provided in 96well plates, each well containing 3 mM polymer in 70% ethanol, Plasmid-DNA (pCMV-Luc) was provided as 0,011 µg/µl stock solution in Buffer F (10 mM NaH2PO4, 225 mM sucrose, pH7.2 (adjusted with NaOH)). 10 µl of polyamines were complexed with to 90 µl of Plasmid-DNA by mixing. 10-15 minutes after complexation, 10 µl of the mixture was used for transfection of HeLa cells resulting in 100 ng of Plasmid-DNA/well.

Determination of luciferase expression: Cells were prepared for quantitation of luciferase 24 h after transfection. Therefore, culture plates were equilibrated to room temperature for ca. 10 min. After discarding the medium cells were washed once with PBS. Cells were lysed using 100 µl of 1×Beetle Lysis Juice (PJK GmbH, Germany) and prepared for luminescence measurement 5 min later. Expression of luciferase was quantified using a TECAN luminescence plate reader.

Example 14

Results for the Transfection of Plasmids

The modified polyamines from example 11 were complexed with plasmid and tested for their transfection properties as described in example 13.

The results of the transfection reactions are described in the table 15 for modified polyamines where the hydrophobic moiety is an aliphatic or cyclic alkyl or an aryl or alkylaryl.

TABLE 15 luminescence measured upon transfection of HeLa cells with a plasmid using certain polyamines wherein the hydrophobic group is an aliphatic alkyl or an aryl. Signals lower than 1000 light units were omitted for clarity, signals over 5000 light units are underlined.

| Polymer | Mol weight in kDa | Hydroxy moiety | Hydrophobic moiety | DOS | % cell viability at certain O/A ratios | | | | | | | |
|---|---|---|---|---|---|---|---|---|---|---|---|---|
| | | | | | 99 | 6 | 2.5 | 1.3 | 0.75 | 0.4 | 0.16 | 0 |
| bPEI | 1.2 | O2 | A12 | 0.5 | | | | | | 1E+04 | 7E+04 | 7E+04 |
| | | O4 | A12 | 0.5 | | | | | 1E+03 | 2E+04 | 6E+04 | 2E+04 |
| | | O6 | A12 | 0.5 | | | | | 1E+04 | 7E+04 | 7E+04 | 1E+04 |
| | | O9 | A12 | 0.5 | | | | 8E+03 | 6E+04 | 2E+05 | 3E+05 | 1E+05 | 4E+04 |
| bPEI | 70 | O6 | A12 | 0.25 | | | | | 6E+03 | | | |
| | | O9 | A9 | 0.5 | | | | | | | 1E+03 | |
| | | O9 | A12 | 0.5 | | | | | 3E+03 | 2E+03 | | |

TABLE 15-continued luminescence measured upon transfection of HeLa cells with a plasmid using certain polyamines wherein the hydrophobic group is an aliphatic alkyl or an aryl. Signals lower than 1000 light units were omitted for clarity, signals over 5000 light units are underlined.

| Polymer | Mol weight in kDa | Hydroxy moiety | Hydrophobic moiety | DOS | 99 | 6 | 2.5 | 1.3 | 0.75 | 0.4 | 0.16 | 0 |
|---|---|---|---|---|---|---|---|---|---|---|---|---|
| lin PEI | 250 | O2 | A6 | 0.5 | | | | | | 7E+03 | 1E+04 | 3E+03 |
| | | O6 | A6 | 0.35 | | | | | 5E+03 | 7E+03 | 1E+03 | 1E+03 |
| | | O6 | A9 | 0.5 | | | | 3E+03 | 4E+03 | 7E+03 | 3E+03 | 1E+03 |
| | | O9 | A3 | 0.35 | 4E+03 | 2E+04 | 4E+04 | 6E+03 | 3E+04 | 3E+03 | 2E+03 | 2E+03 |
| | | O9 | A6 | 0.35 | 2E+03 | 6E+03 | 3E+04 | 7E+04 | 7E+04 | 1E+04 | 8E+03 | 3E+03 |
| | | O9 | A9 | 0.25 | | 1E+05 | 1E+04 | 2E+03 | 2E+03 | | 2E+03 | |
| | | O9 | A12 | 0.35 | 1E+03 | 2E+04 | 2E+04 | 1E+04 | 1E+04 | 4E+03 | 1E+03 | |
| bPEI | 1.2 | O6 | BB | 0.5 | | | | 1E+03 | 2E+03 | 3E+03 | 2E+03 | 1E+03 |
| | | O6 | 4-IPBB | 0.5 | | | 1E+03 | | 2E+03 | 1E+03 | 2E+03 | |
| bPEI | 70 | O2 | 4-IPBB | 0.35 | 2E+03 | | | 6E+03 | 1E+04 | 6E+03 | | 7E+03 |
| | | O4 | 4-IPBB | 0.25 | | | | 3E+03 | 3E+03 | 5E+03 | 2E+04 | 6E+03 |
| | | O9 | BB | 0.5 | | | | | | 3E+03 | 1E+04 | |
| | | O9 | 4-IPBB | 0.5 | | | 3E+03 | 6E+03 | 1E+04 | 2E+04 | 4E+03 | |
| lin PEI | 250 | O2 | BB | 0.35 | 3E+03 | | 7E+04 | 7E+03 | 6E+04 | 7E+04 | 9E+04 | 1E+04 |
| | | O2 | 4-IPBB | 0.5 | | | 5E+03 | 9E+03 | 3E+04 | 4E+03 | 3E+03 | |
| | | O4 | BB | 0.35 | 3E+03 | 6E+03 | 2E+04 | 2E+04 | 1E+05 | 4E+04 | 2E+04 | 2E+03 |
| | | O4 | 4-IPBB | 0.5 | | 3E+04 | 2E+05 | 5E+04 | 5E+04 | 1E+04 | 2E+03 | 2E+03 |
| | | O4 | B2CHE | 0.5 | | 3E+03 | | 1E+03 | 4E+03 | 1E+04 | 5E+04 | 9E+03 |
| | | O6 | BB | 0.35 | | 1E+03 | | 3E+03 | 8E+04 | 1E+04 | 2E+04 | 2E+04 |
| | | O6 | 4-IPBB | 0.35 | | | 3E+03 | | 3E+04 | | 5E+03 | 5E+03 |
| | | O9 | 2BEB | 0.25 | 5E+04 | 5E+04 | 9E+04 | 4E+04 | 1E+05 | 3E+04 | 2E+04 | |
| | | O9 | B2CHE | 0.25 | 1E+04 | 5E+04 | 1E+05 | 3E+04 | 3E+04 | 2E+04 | 4E+03 | 6E+03 |

The data of this table 15 demonstrate that many of the hydroxylated, hydrophobized polyamines are capable of transfecting a plasmid into cells. The hydrophilic group was selected from aliphatic or cyclic alkyl or various aryl moieties and all resulted in the formation of active carriers regardless of their structural differences.

The active carriers were formed from polyamines having widely different molecular weights, different architecture (linear or branched). It is also apparent from the data that the hydroxyl and hydrophobic components act synergistically, while single modifications contribute little to the carrier properties.

Example 15

Synthesis of Various Hydroxylated, Hydrophobized Oligospermines and Homologues Thereof Starting from commercially available 1,4-diamino butane (1) the central intermediate 21 was obtained in a three step synthesis.

Scheme 1: Synthetic route to the central intermediate 21.

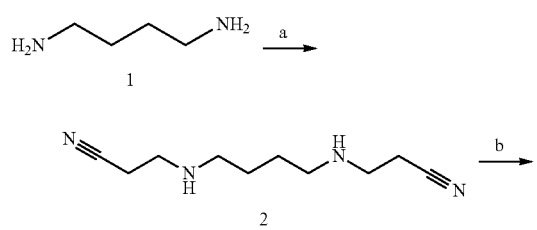

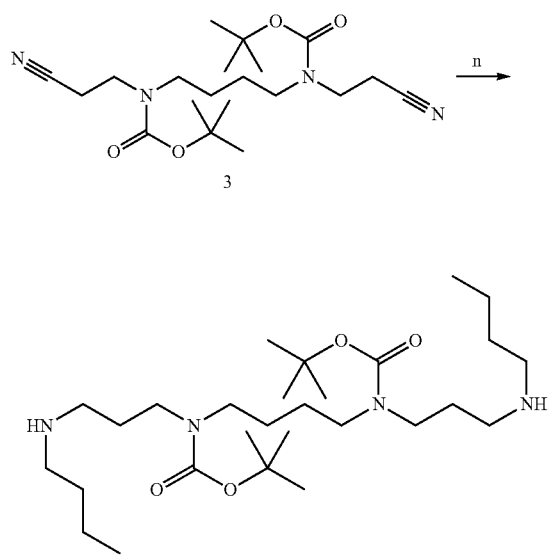

Compound 2 is easily accessible by addition of acrylonitrile to 1,4-diamino butane (1) in step a. Following this, two boc-protection groups were introduced into the molecule, in leading to compound 3. The nitrile 3 was then reduced with hydrogen in the presence of excess butylamine to give 21.

Scheme 2: The oligomerization reaction

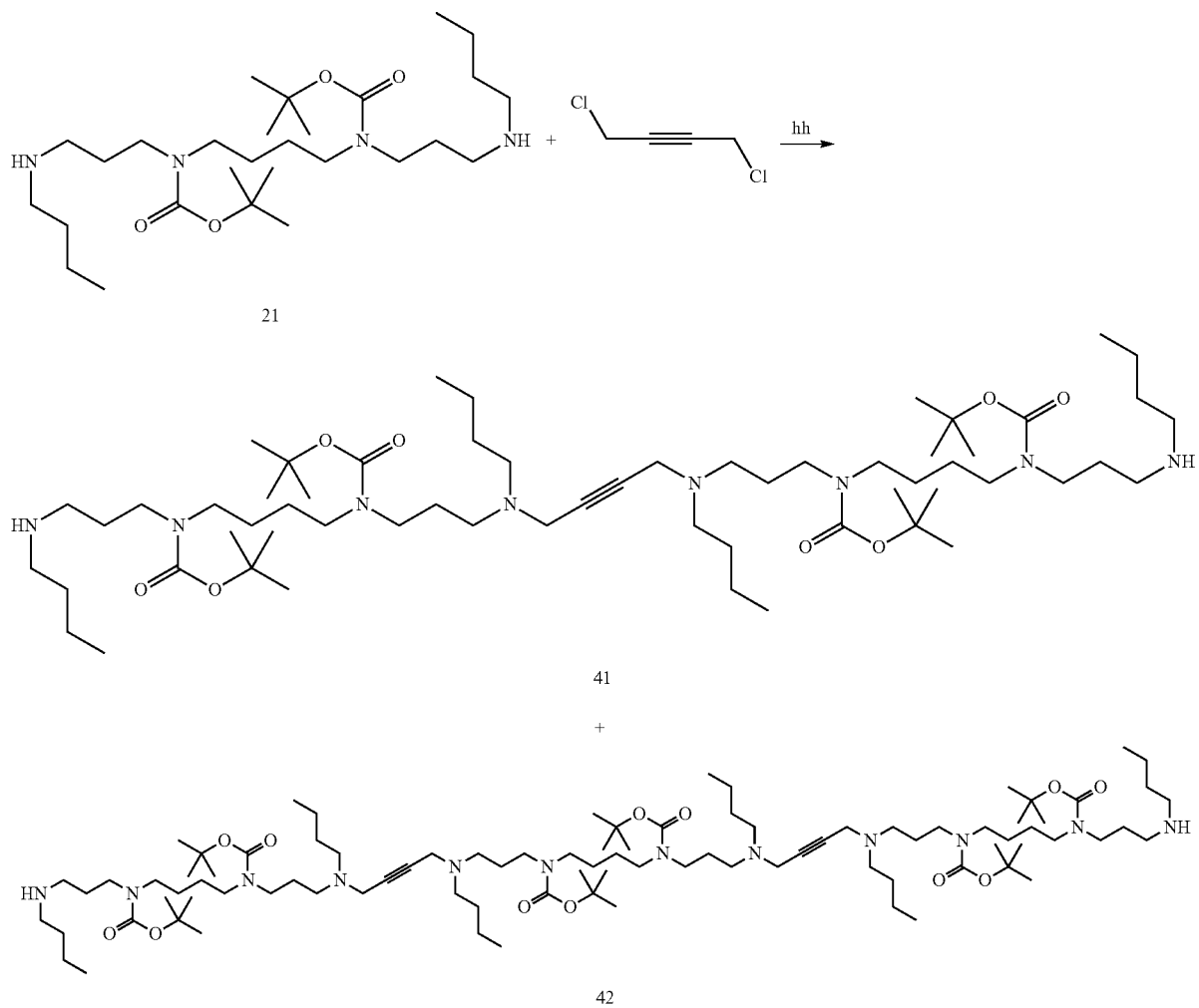

For the formation of oligospermins, 21 was reacted with 1,4-dichlorobut-2-in under standard alkylation conditions to give dimer 41, trimer 42 and a series of longer oligomers. Unfortunately the N—CH$_2$—C≡C moiety is not stable and susceptible to cleavage. Therefore the triple bond of compounds 41, 42 or the higher oligomers were reduced followed by removal of the Boc-groups.

Analogue reactions were carried out using 1,5-diaminopentane or 1,6-diaminohexane as the starting material 1, leading to a series of oligospermine homologues or polyalkylenimines wherein the variable x denoting the spacing between the nitrogen groups oscillates between 2 and 3, 2 and 4, or 2 and 5.

In addition to the formation of the oligospermine homologues, the size of the hydrophobic substituents was systematically varied between butyl (as illustrated in this example), ethyl, hexyl and decyl, yielding a matrix of polyalkylenimines having variations in their alkylen groups, their hydrophobic substituents and their degree of oligomerization.

The oligospermines and their homologues (altogether the polyalkylenimines of this example) were desalted using Sephadex G25 and the individual oligomers were purified using ion exchange chromatography on CM-Sepharose Fast Flow and SP-Sepharose Fast Flow. The oligospermines elute from the ion exchange column according to their degree of polymerization and are denoted with roman numerals I to XII, whereby higher numbers stand for longer oligomers. The degree of polymerization was determined with mass spectroscopy and ranged from trimers through to about eicosamers.

Fractions containing the separated oligomers were extracted from the buffer using dichlormethan under basic conditions, dried under vacuum and dissolved in absolute ethanol at a concentration of 250 mM nitrogen.

In a subsequent step, samples of 50 μmol of each oligomer were derivatized with 0, 10, 15, 20 or 25 μmol of the ω-bromoalkanols O2, O4, O6, O9 or O12 using the general protocol of example 11.

Example 16

Transfection of Cells Using Hydroxyl-Hydrocarbon-Oligospermines

The transfection testing of the various hydroxylated and hydrophobized oligospermines and their respective homologues was performed using the siRNA targeting PLK-1, the HeLa cells and the cell culture conditions and assays described in the examples 2 to 7. The following table 16 is a list of the results obtained using the hydroxyl-hydrocarbon-oligospermines as transfectants for siRNA.

solution of the modified polyamine were rapidly mixed with 4.1 ml of either buffer. A colloid forms and the particle size and the zeta potential of the dispersed phase were determined using a MALVERN Zetasizer 3000HSA.

TABLE 16

Inhition of the cell viability of HeLa cells upon transfection of a cytotoxic siRNA using hydroxylated, hydrophobized oligospermines. Numerals x denote the oscillating lengths of the alkylen units according to formula (1), the roman numerals for the oligomers denote the degree of polymerization of the oligomers. The numbers in the table show the remaining cell viability, low numbers indicate an efficient transfection.

| | | | % substitution with O9 | | | | | % substitution with O12 | | | | |
|---|---|---|---|---|---|---|---|---|---|---|---|---|
| x | alkyl | oligomer | 0 | 20 | 30 | 40 | 50 | 0 | 20 | 30 | 40 | 50 |
| 2, 3 | ethyl | I | 50 | 62 | 70 | 74 | 70 | 73 | 82 | 61 | 63 | 60 |
| | | II | 26 | 33 | 42 | 44 | 44 | 70 | 76 | 42 | 29 | 35 |
| | | III | 22 | 26 | 32 | 51 | 37 | 69 | 66 | 20 | 19 | 45 |
| | | IV | 87 | 104 | 108 | 109 | 104 | 100 | 60 | 59 | 76 | 102 |
| | | VIII | 58 | 44 | 55 | 50 | 65 | 75 | 102 | 78 | 73 | 71 |
| | | IX | 34 | 33 | 36 | 44 | 53 | 105 | 103 | 52 | 47 | 39 |
| | | X | 66 | 54 | 55 | 55 | 59 | 99 | 88 | 84 | 68 | 62 |
| 2, 4 | ethyl | VI | 54 | 55 | 54 | 69 | 74 | 101 | 95 | 91 | 94 | 104 |
| | | VII | 65 | 65 | 83 | 90 | 89 | 89 | 73 | 84 | 96 | 96 |
| | | VIII | 68 | 79 | 82 | 76 | 77 | 82 | 58 | 44 | 27 | 40 |
| | | iX | 76 | 74 | 73 | 58 | 64 | 85 | 34 | 38 | 29 | 35 |
| 2, 5 | ethyl | I | 35 | 28 | 33 | 40 | 16 | 43 | 40 | 25 | 13 | 45 |
| | | II | 37 | 49 | 66 | 53 | 60 | 77 | 81 | 60 | 42 | 44 |
| | | III | 83 | 53 | 79 | 75 | 94 | 81 | 79 | 60 | 33 | 46 |
| | | IV | 39 | 69 | 90 | 84 | 95 | 92 | 71 | 39 | 30 | 42 |
| | | V | 103 | 104 | 106 | 112 | 108 | 109 | 104 | 105 | 103 | 107 |
| | | VI | 103 | 98 | 99 | 98 | 45 | 107 | 103 | 103 | 104 | 107 |
| | | VII | 88 | 93 | 93 | 97 | 95 | 95 | 96 | 96 | 51 | 29 |
| | | VIII | 90 | 93 | 91 | 101 | 90 | 103 | 93 | 95 | 96 | 45 |
| 2, 4 | butyl | III | 75 | 88 | 84 | 99 | 92 | 101 | 101 | 103 | 106 | 104 |
| | | IV | 32 | 55 | 80 | 94 | 85 | 94 | 102 | 106 | 104 | 119 |
| | | V | 87 | 48 | 61 | 22 | 22 | 73 | 86 | 97 | 92 | 101 |
| 2, 3 | hexyl | VI + VII | 90 | 91 | 93 | 87 | 92 | 102 | 99 | 99 | 99 | 99 |
| | | VIII + IX | 103 | 103 | 16 | 1 | 2 | 103 | 103 | 101 | 99 | 101 |
| | | X | 99 | 106 | 109 | 107 | 100 | 108 | 106 | 102 | 103 | 111 |
| | | XI | 92 | 99 | 0 | 0 | 2 | 113 | 99 | 99 | 100 | 106 |
| | | XII | 89 | 106 | 66 | 99 | 91 | 113 | 111 | 104 | 102 | 111 |
| 2, 4 | hexyl | VI | 102 | 99 | 94 | 1 | 5 | 105 | 92 | 39 | 0 | 6 |
| | | VII | 96 | 15 | 0 | 0 | 3 | 94 | 89 | 97 | 101 | 107 |
| | | VIII | 57 | 0 | 2 | 85 | 58 | 104 | 103 | 107 | 106 | 106 |

The data of this table 16 demonstrate that many of the hydroxylated, hydrophobized oligospermines are capable of transfecting cells. The active carriers were formed from oligospermines having widely different molecular weights and are of different molecular architecture as the spacing between the nitrogen atoms was varied. It is also apparent from the data that the hydroxyl and hydrophobic components act synergistically, as the alkylated oligospermins display little activity in the cell transfection while the introduction of the hydroxyl moieties lead to active carrier structures.

Example 17

Neutral and Anionic Particles from Modified Polyamines and Nucleic Acid Buffers containing 280 mM sucrose, 10 mM sodium dihydrogenphosphate and 3 mM sodium hydroxide (pH6.5) or 7 mM sodium hydroxide (pH7.2) was prepared. Stock solutions of the siRNA from example 5 were prepared in the buffers to obtain 10 fold the concentrations listed in table 20.

The modified polyamine of example 8 was provided as a solution having a concentration of 56 mM modified polyamine (as mono-mM) in 96% ethanol; 50 µl of said 900 µl of the various siRNA solutions were rapidly mixed with the dispersions of the modified polyamine in buffer so to obtain the N/P ratios listed in table 17 and size and zeta potential were recorded again.

TABLE 17

Size and zeta potential of complexes between a modified polyamine and siRNA having various ratios of N/P.

| polyamine [µM] | siRNA [µM] | N/P | pH6.5 Size [nm] | Zeta potential [mV] | pH7.2 Size [nm] | Zeta potential [mV] |
|---|---|---|---|---|---|---|
| 560 | 6.2 | 2 | 398 | −18.2 | 605 | −15 |
| 560 | 3.1 | 4 | 467 | −12.1 | 626 | −14 |
| 560 | 2.1 | 6 | 708 | −12.7 | 872 | −5.4 |
| 560 | 1.4 | 9 | 923 | 3.3 | 1098 | 1.7 |
| 560 | 1.0 | 12 | 1145 | 1.1 | 971 | 1.7 |
| 560 | 0.8 | 15 | 914 | 2.8 | 783 | −2.8 |
| 560 | 0.6 | 20 | 614 | −0.2 | 553 | 2 |
| 560 | 0.4 | 30 | 541 | 1.2 | 562 | 2.1 |
| 560 | 0.0 | 99 | 428 | 2.8 | 624 | 2.8 |

General observations: the modified polyamines do from particles having a size of about 500 nm and an almost neutral zeta potential. Addition of small amounts of siRNA resulting in N/P ratios of 20 or higher do not substantially alter the size or surface charge of the particles. However, addition of high amounts of siRNA led to the formation of anionic particles of about the same size. Intermediate amounts of siRNA (NP=9 . . . 15) lead to intermediate zeta potential and the formation of aggregates. The systems behavior can be understood as the interaction of two polyelectrolytes of opposite charge, where aggregation occurs under the conditions of charge neutralization as described in Endert et al. (2004) "Nanocapsules from liposomal templates", pp. 238-248 in Carrier Based Drug Delivery, Oxford University Press.

Example 18

Transfection with Anionic or Neutral Complexes

Complexes were produced from a modified polyamine and an siRNA targeting PLK-1 or a non-targeting control siRNA as in example 17. The N/P ratios were 3 and 20 and the pH of the buffer was 7.2. The resulting materials were adjusted to equal concentrations of siRNA and tested for their ability to transfect HeLa-cells under the conditions described in the examples 2 to 7.

The resulting EC50 values and signal:noise ratios are listed in the table 18 below.

TABLE 18 transfection properties of complexes having different N/P ratios.

| N/P ratio | EC50 PLK-1 [nM] | EC50 Control [nM] | Signal:noise ratio |
|---|---|---|---|
| 20 | 12.5 | 118 | 9.4 |
| 3 | 36.1 | 500 | 14 |

The data demonstrate that both the neutral complexes having a N/P of 20 or the anionic complexes having an N/P of 3 are active transfectants. The EC50 value of the N/P=3 complex indicates a somewhat lower activity of the anionic materials. However, a critical inspection of the data needs to take into account the presence of some non-complexed siRNA in these complexes, as the charge reversal was shown to be complete at N/P of about 6. The signal-to-noise ratio of the anionic complexes appears to be even higher than that of the neutral materials.

The content of European patent application No. 12 006 913.3, filed on Oct. 2, 2012, the priority of which is claimed, is herewith incorporated by reference including all claims and entire description.

The invention claimed is:

1. A polyalkylenimine derivative having one or more hydroxyalkyl substituents comprising from 4 to 40 carbon atoms, and one or more hydrophobic substituents selected from hydrocarbon substituents having at least 2 carbon atoms, wherein each of said hydrophobic substituents may be or may comprise an alkyl group and/or each of said hydrophobic substituents may be or may comprise an aryl group.

2. An hydroxyalkyl-alkyl-polyamine derivative according to claim 1, wherein said hydroxyalkyl-alkyl-polyamine has one type of said hydroxyalkyl moiety and one type of said alkyl moiety, and the sum of carbon atoms in the type of hydroxyalkyl moiety and the type of alkyl moiety is between 10 and 30.

3. The polyalkylenimine derivative of claim 1 wherein said one or more hydrophobic substituents selected from hydrocarbon substituents having at least 6 to 40 carbon atoms.

4. The polyalkylenimine derivative according to claim 2, wherein said sum of carbon atoms of the hydroxyalkyl and alkyl moieties is between 15 and 25.

* * * * *